US009839674B2

(12) United States Patent
Salford et al.

(10) Patent No.: US 9,839,674 B2
(45) Date of Patent: Dec. 12, 2017

(54) METHODS OF INDUCING INDOLAMINE 2,3—DIOXYGENASE (IDO)

(71) Applicant: IDOGEN AB, Lund (SE)

(72) Inventors: Leif Salford, Lund (SE); Hans Olov Sjogren, Lund (SE); Bengt Widegren, Lund (SE)

(73) Assignee: Idogen AB, Lund (SE)

( * ) Notice: Subject to any disclaimer, the term of this patent is extended or adjusted under 35 U.S.C. 154(b) by 0 days.

(21) Appl. No.: 14/553,098

(22) Filed: Nov. 25, 2014

(65) Prior Publication Data

US 2015/0182592 A1 Jul. 2, 2015

Related U.S. Application Data

(62) Division of application No. 13/997,356, filed as application No. PCT/SE2011/051544 on Dec. 20, 2011, now abandoned.

(30) Foreign Application Priority Data

Dec. 22, 2010 (SE) ...................... 1051356

(51) Int. Cl.
| | | |
|---|---|---|
| *A61K 31/19* | (2006.01) | |
| *A61K 31/56* | (2006.01) | |
| *A61K 31/593* | (2006.01) | |
| *A61K 31/7068* | (2006.01) | |
| *A61K 38/24* | (2006.01) | |
| *A61K 38/21* | (2006.01) | |
| *A61K 45/06* | (2006.01) | |
| *A61K 38/18* | (2006.01) | |

(52) U.S. Cl.
CPC .............. *A61K 38/24* (2013.01); *A61K 31/19* (2013.01); *A61K 31/56* (2013.01); *A61K 31/593* (2013.01); *A61K 31/7068* (2013.01); *A61K 38/1841* (2013.01); *A61K 38/212* (2013.01); *A61K 38/217* (2013.01); *A61K 45/06* (2013.01)

(58) Field of Classification Search
CPC ...... A61K 31/19; A61K 31/593; A61K 31/56; A61K 38/24; A61K 38/212; A61K 38/217; A61K 45/06; A61K 2300/00
See application file for complete search history.

(56) References Cited

U.S. PATENT DOCUMENTS

| | | |
|---|---|---|
| 6,518,012 B1 | 2/2003 | Tomasi |
| 8,372,870 B2 | 2/2013 | Combs et al. |
| 2004/0109846 A1 | 6/2004 | Rubinfeld et al. |
| 2008/0108559 A1 | 5/2008 | DiMartino |
| 2009/0117074 A1 | 5/2009 | Maier et al. |
| 2011/0300142 A1 | 12/2011 | Salford et al. |

FOREIGN PATENT DOCUMENTS

| | | |
|---|---|---|
| WO | 2006105979 | 10/2006 |
| WO | 2006122150 | 11/2006 |
| WO | 2007017065 | 2/2007 |
| WO | 2008147283 | 12/2008 |

OTHER PUBLICATIONS

Caplen, H.S. et al, Differential regulation of a cellular gene by human intereferon-gamma and interferon-alpha. Journal of Biological Chemistry, 1988, vol. 263, No. 1, p. 332-339.*
Takikawa, O, et al. Mechanism of interferon-gamma action. Journal of Biological Chemistry, 1988, vol. 263, No. 4, p. 2041-2048.*
Tarte et al. Blood Nov. 16, 2006, vol. 108, No. 11, Part 1, p. 924A, "Influence of inflammatory factors produced during graft-versus-host disease on immunological properties of mesenchymal stem cells (MSC)."
Popp et al. Transplant Immunology 2008, vol. 20, p. 55-60, "Mesenchymal stem cells can induce long-term acceptance of solid organ allografts in synergy with low-dose mycophenolate."
Oxenkrug., Annals of the New York Academy of Science 2007, vol. 1122, p. 35-49, "Genetic and Hormonal Regulation of Tryptophan-Kynurenine Metabolism, Implications for Vascular Cognitive Impairment, Major Depressive Disorder, and Aging."
Kwidzinski et al. The FASEB Journal express article, Published online Jun. 6, 2005, 19 Pages, "Indolamine 2,3-dioxygenase is expressed in the CNS and down-regulates autoimmune inflammation."
International Search Report for PCT/SE2011/051544, Completed by the Swedish Patent Office on Mar. 2, 2012, 7 Pages.
Uyttenhove et al. Nature Medicine Oct. 2003, vol. 9, No. 10, p. 1269-1274, "Evidence for a tumoral immune resistance mechanism based on tryptophan degradation by indoleamine 2,3-dioxygenase."
Mellor et al. Nature Reviews Immunology Oct. 2004, vol. 4, p. 762-774, "IDO Expression by Dendritic Cells: Tolerance and Tryptophan Catabolism."
Munn et al. The Journal of Clinical Investigation Jul. 2004, vol. 114, No. 2, p. 280-290, "Expression of Indoleamine 2,3-dioxygenase by plasmacytoid dendritic cells in tumor-draining lymph nodes."
Fallarino et al. Current Drug Metabolism 2007, vol. 8, p. 209-216, "Tryptophan Catabolism in IDO Plasmacytoid Dendritic Cells."
Hissong et al. J. Interferon Cytokine Res. 1997, vol. 17, p. 387-393, "Potentiation of interferon-induced indoleamine 2,3-dioxygenase mRNA in human mononuclear phagocytes by lipopolysaccharide and interleukin-1."

(Continued)

*Primary Examiner* — Robert Landsman
*Assistant Examiner* — Bruce D Hissong
(74) *Attorney, Agent, or Firm* — Dentons US LLP

(57) ABSTRACT

A composition and method for using a composition, the composition having at least two compounds, each of which induces indolamine 2,3-dioxygenase, for the treatment of an autoimmune disorder or disease or immune rejection of transplants or gene therapeutically modified cells, wherein the inducers have different mechanism of action and wherein the composition gives rise to a synergistic effect on the IDO levels.

11 Claims, 18 Drawing Sheets

(56) References Cited

OTHER PUBLICATIONS

Braun et al., A two-step induction of indoleamine 2,3 dioxygenase (IDO) activity during dendritic-cell maturation, Blood, 2005, pp. 2375-2381, vol. 106, No. 7.
Currier et al., Tumor Necrosis Factor-α and Lipopolysaccharide Enhance Interferon-Induced Antichlamydial Indoleamine Dioxygenase Activity Independently, J of Interferon and Cytokine Res., 2000, pp. 369-376, vol. 20.
Kahler et al., T Cell Regulatory Plasmacytoid Dendritic Cells Expressing Indoleamine 2,3 Dioxygenase, Handb Exp Pharmacol., 2009, pp. 165-196, vol. 188.
Kawaguchi et al., Priming of peripheral monocytes with prolactin (PRL) sensitizes IFN-γ signaling, J of Reproductive Immunology, 2008, pp. 117-125, vol. 77.
Lei et al., Upregulation of Placental Indoleamine 2,3-Dioxygenase by Human Chorionic Gonadotropin, Biology of Reproduction, 2007, pp. 639-644, vol. 76.
Robinson et al., The Role of IFN-γ and TNF-α-Responsive Regulatory Elements in the Synergistic Induction of Indoleamine Dioxygenase, J Interferon Cytokine Res., 2005, pp. 20-30, vol. 25, No. 1.
Petska et al., The Interferons: 50 Years after Their Discovery, There is Much More to Learn, J Biol Chem., 2007, pp. 20047-20051, vol. 282, No. 28.
Schmidt et al., New insights into IDO biology in bacterial and viral infections, Frontiers in Immunol., 2014, pp. 1-12, vol. 5, No. 384.
Heyes, Quinolinic Acid and Inflammation, Annals NY Acad Sci, 2006, vol. 679, No. 1, pp. 211-216.
Takikawa, Biochemical and medical aspect of the indoleamine 2,3-dioxygenase-initiated l-tryptophan metabolism, Biochem Biophys Res Comm, 2005, vol. 338, pp. 12-19.
Best et al., Interferon gamma inhibits luteinized human granulosa cell steroid production in vitro, Am J Obstet Gynecol, 1995, vol. 172, No. 5, pp. 1505-1510.
European Partial Search Report dated Sep. 6, 2017 in related Application No. EP17166929.4 filed Apr. 18, 2017 (27 pages).
Glauben et al., Histone Deacetylases: novel targets for prevention of colitis-associated cancer in mice, Gut, 2008, vol. 57, No. 5, pp. 613-622, Abstract Only (2 pages).
Jang et al., Influence of valproic acid on cytokine expression of spleen cells and acute graft-versus-host-disease in a murine model, Blood, 2005, vol. 106, No. 11, Part 2, p. 148B, Abstract Only (2 pages).
Larsen, et al., Inhibition of histone deacetylases prevents cytokine-induced toxicity in beta cells, Diabetologia, 2007, vol. 50, No. 4, pp. 779-789.
Leng, et al., Inhibition of graft-versus-host disease (GVHD) by histone deacetylase inhibitor (HDAC) SAHA leads to downregulation of STAT1 activation, Blood, 2005, vol. 106, No. 11, p. 1311, Abstract Only (1 page).
Mora-Garcia et al., Up-regulation of HLA class-I antigen expression and antigen-specific CTL response in cervical cancer cells by the demethylating agent hydralazine and the histone deacetylase inhibitor valproic acid, Journal of Translational Medicine, 2006, vol. 4, No. 55 (14 pages).
Zhang et al., Valproic acid attenuates inflammation in experimental autoimmune neuritis, Cell. Mol. Life Sci., 2008, vol. 65, No. 24, pp. 4055-4065.

\* cited by examiner

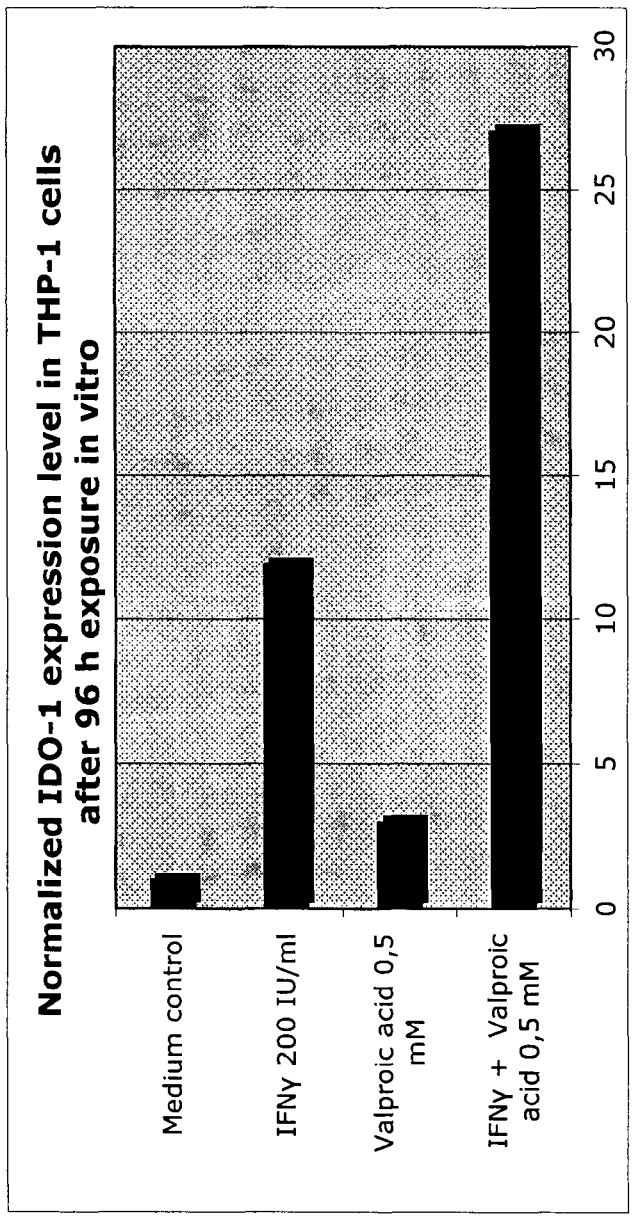

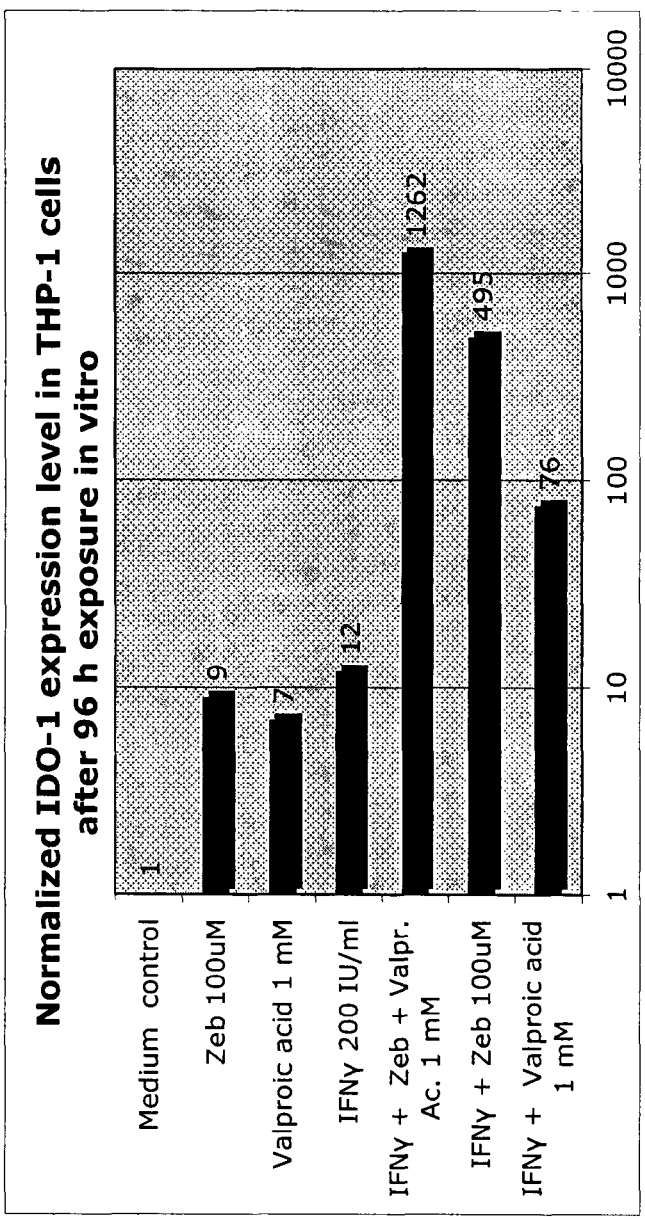

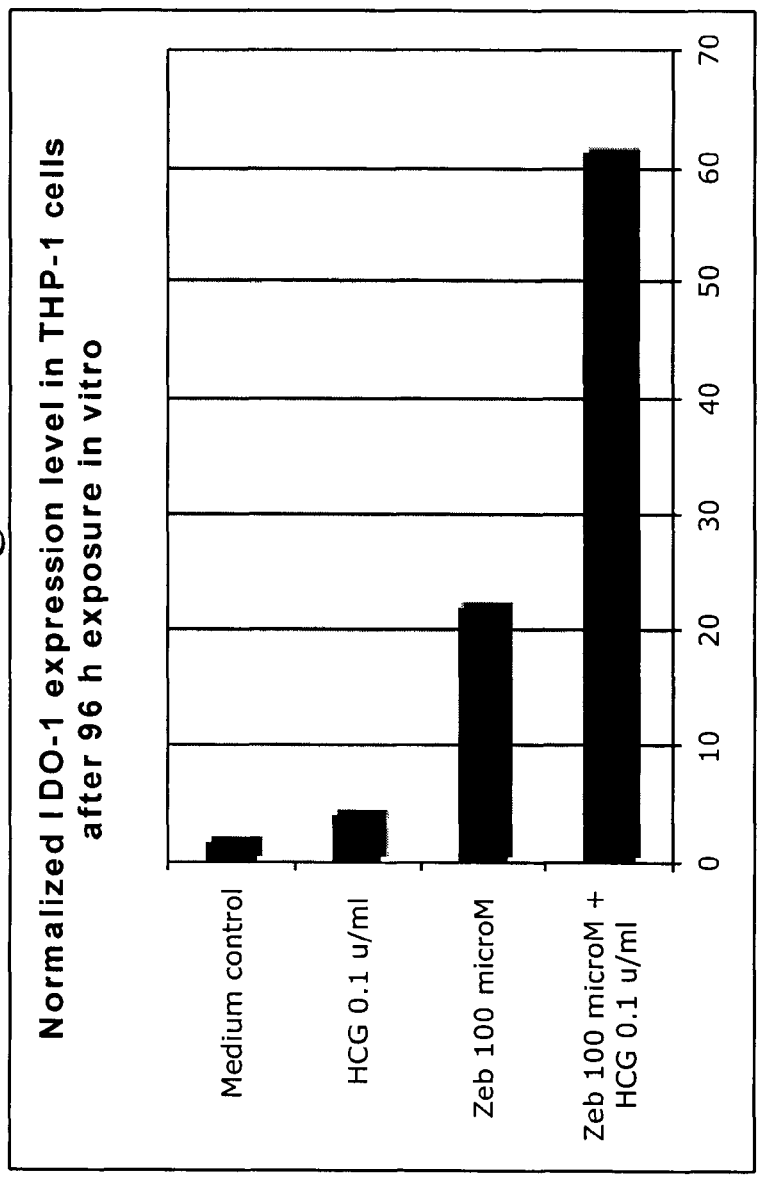

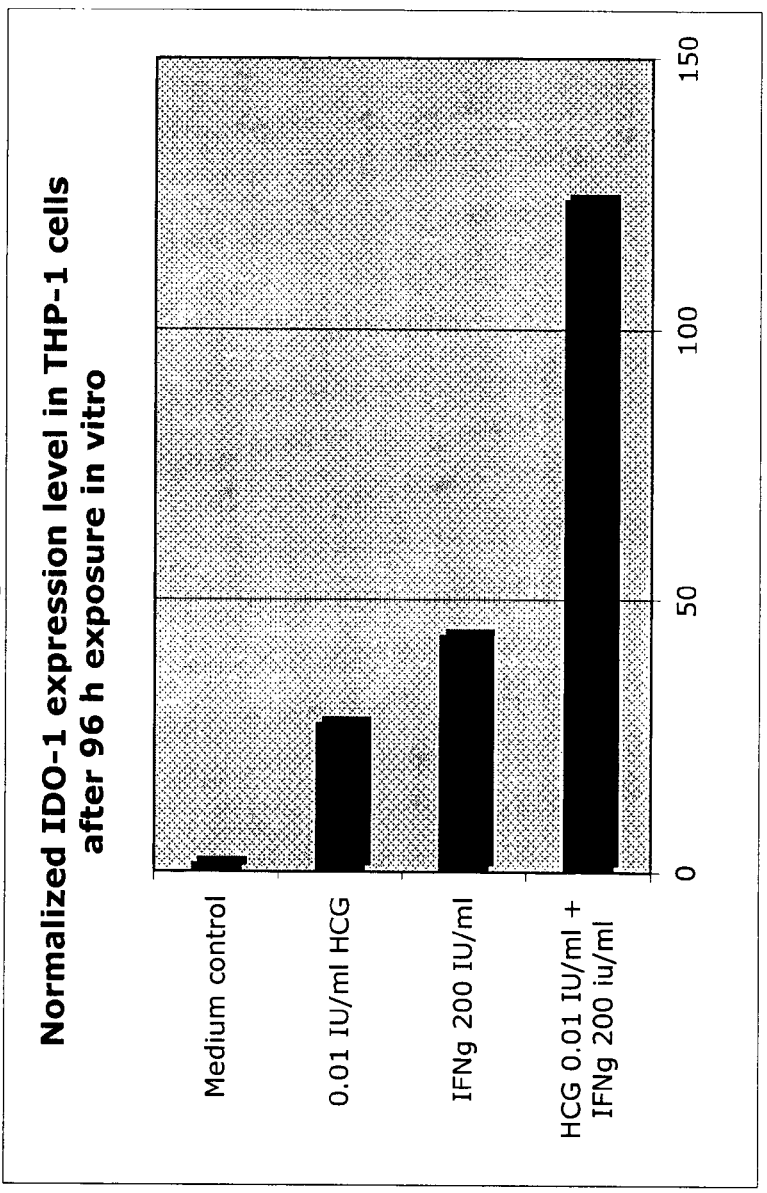

Fig. 5
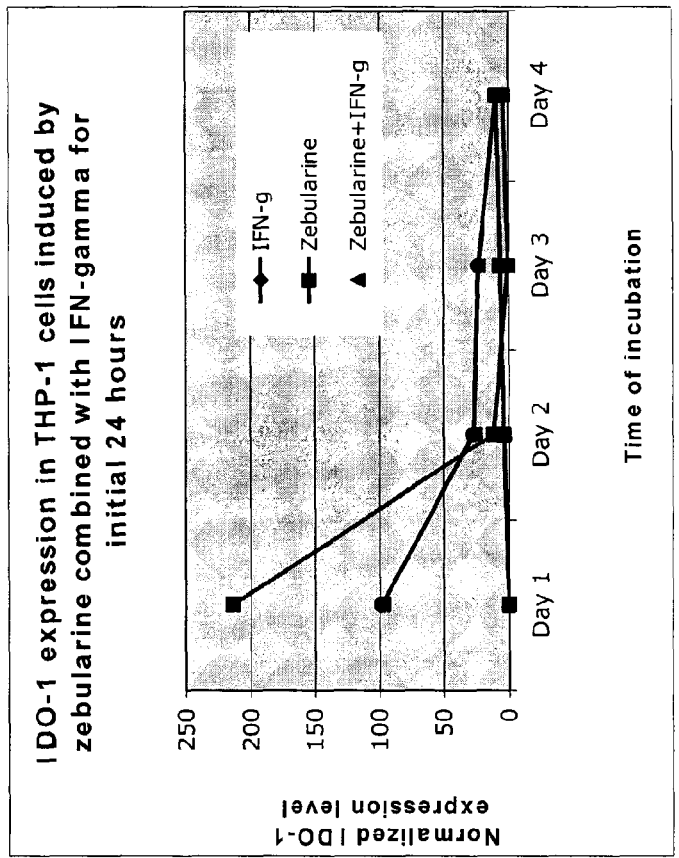
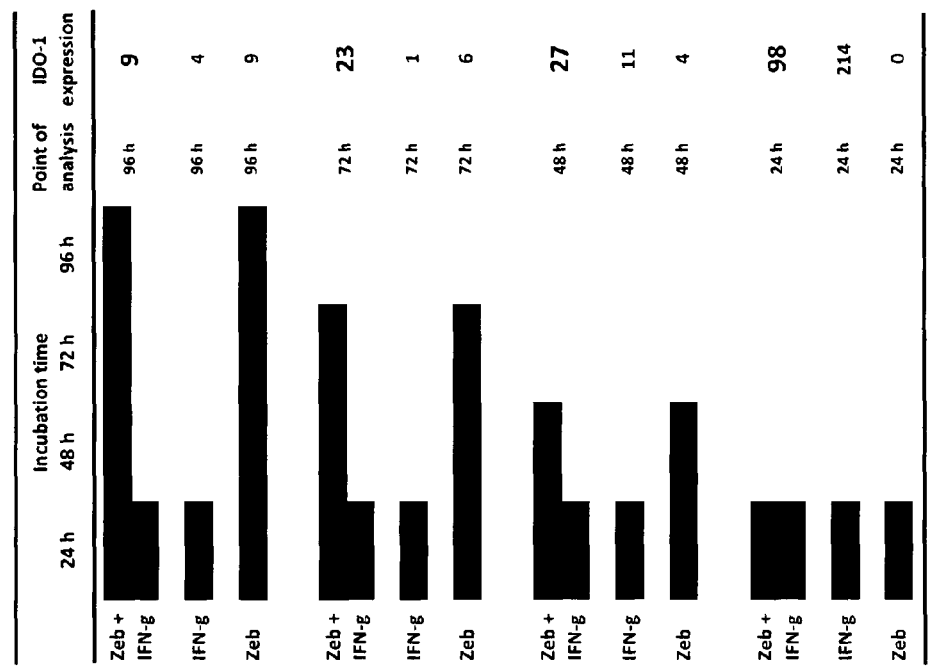

Normalized IDO1 expression in THP-1 human monocytic cells after 120 hrs of culture and exposure to 100 uM zebularine for the entire period, to 100 iu/ml IFN-γ in the interval 72-96 h, and to 20 ng/ml TGF-β1 during the last 24 h, 96-120 h, as indicated Fig. 14
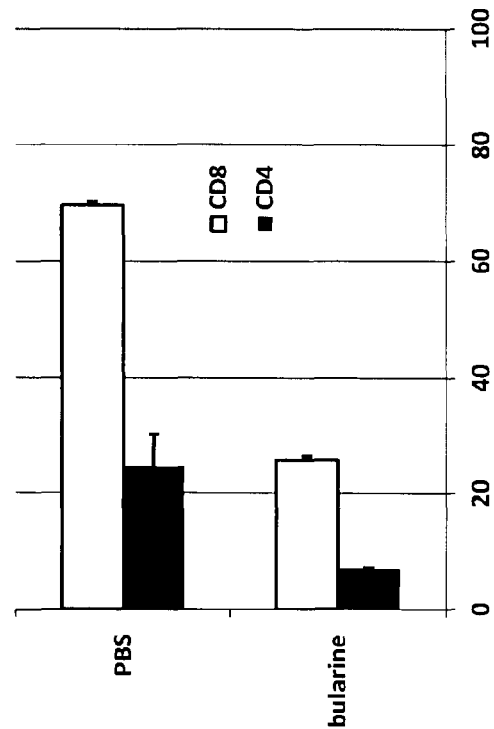
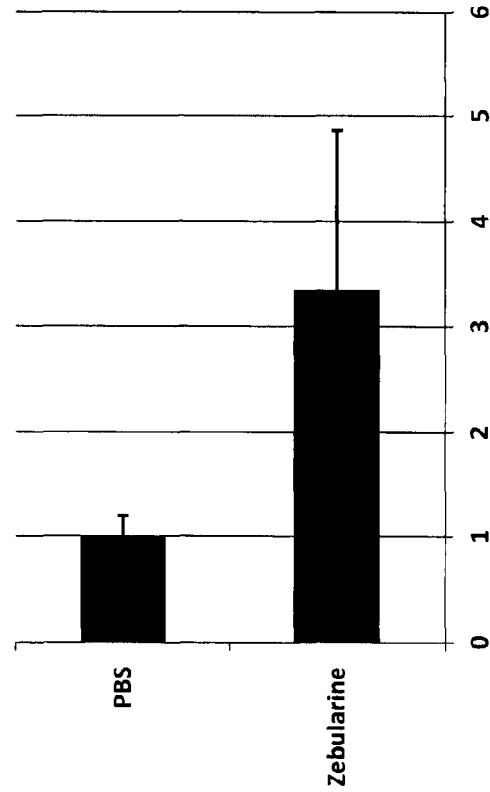

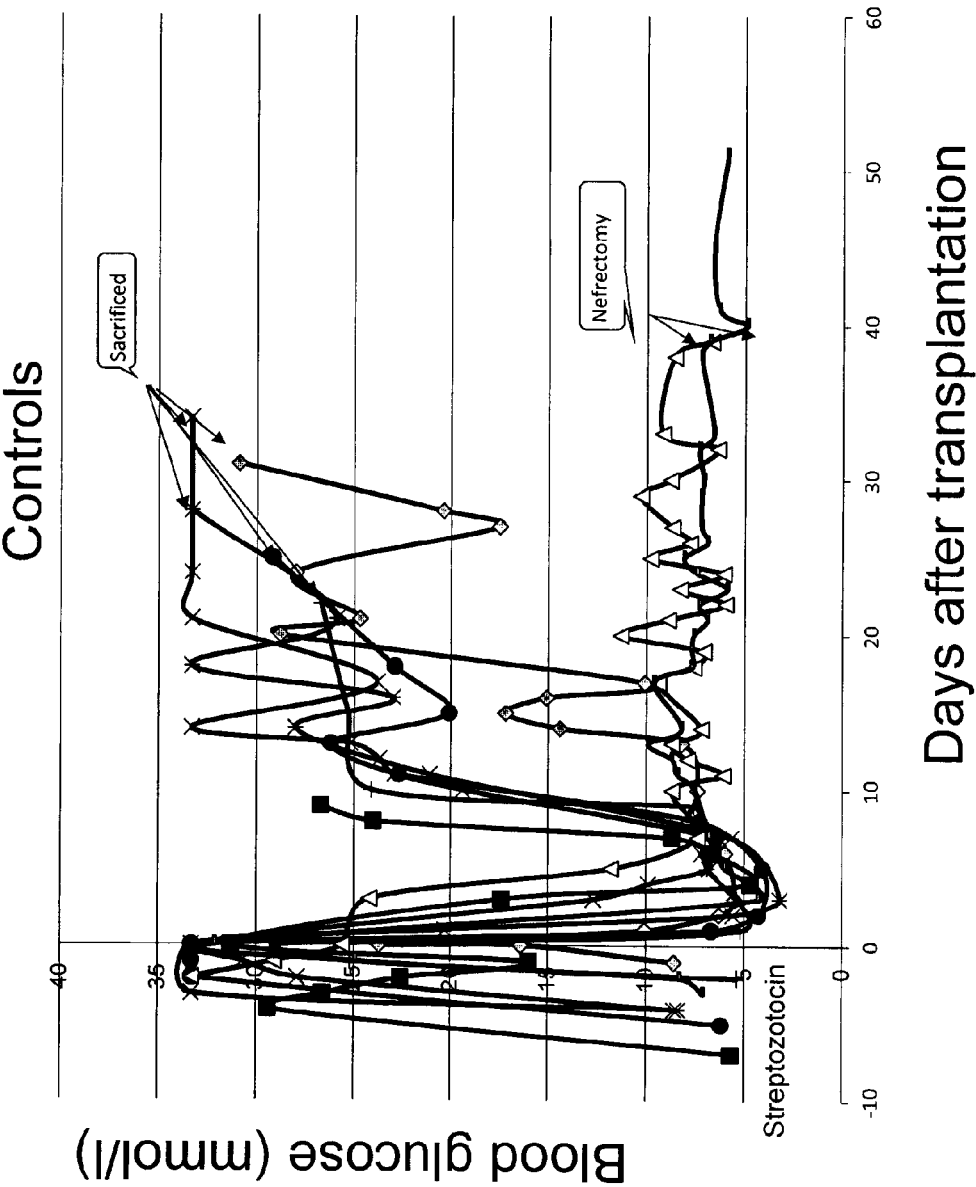

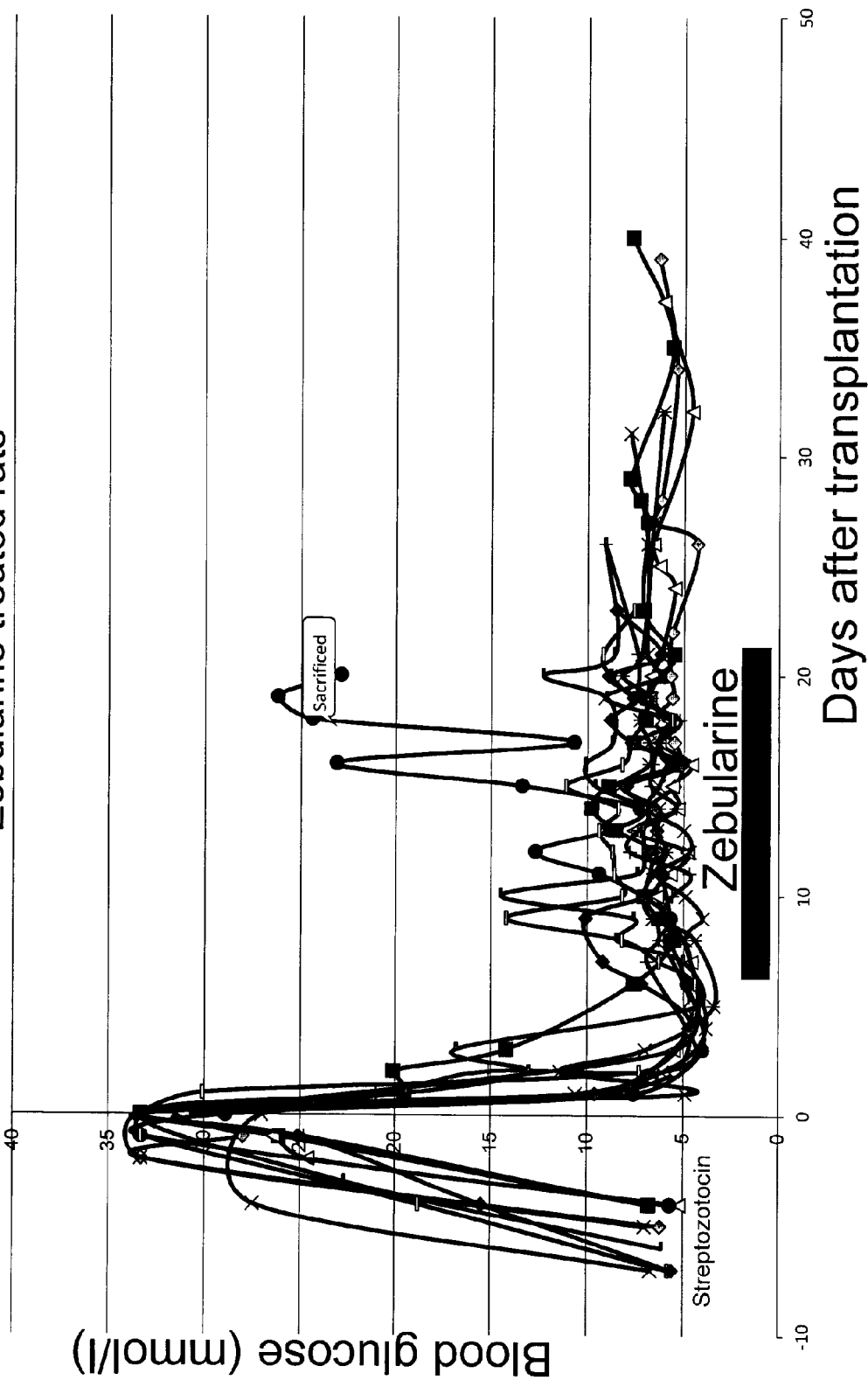

SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: PCR Primer

<400> SEQUENCE: 1
ggcaaactgg aagaaaaagg                                           20

<210> SEQ ID NO 2
<211> LENGTH: 22
<212> TYPE: DNA
<213> ORGANISM: Artificial Sequence
<220> FEATURE:
<223> OTHER INFORMATION: PCR Primer

<400> SEQUENCE: 2
cagacaaata tatgcgaaga ac                                        22

<210> SEQ ID NO 3
<211> LENGTH: 21
<212> TYPE: DNA
<213> ORGANISM: Artificial Sequence
<220> FEATURE:
<223> OTHER INFORMATION: PCR Primer

<400> SEQUENCE: 3
caagcttgct ggtgaaaagg a                                         21

<210> SEQ ID NO 4
<211> LENGTH: 21
<212> TYPE: DNA
<213> ORGANISM: Artificial Sequence
<220> FEATURE:
<223> OTHER INFORMATION: PCR Primer

<400> SEQUENCE: 4
actaagcaga tggccacaga a                                         21

<210> SEQ ID NO 5
<211> LENGTH: 23
<212> TYPE: DNA
<213> ORGANISM: Artificial Sequence
<220> FEATURE:
<223> OTHER INFORMATION: PCR Primer

<400> SEQUENCE: 5
agtccgtgag tttgtcctttt caa                                      23

<210> SEQ ID NO 6
<211> LENGTH: 22
<212> TYPE: DNA
<213> ORGANISM: Artificial Sequence
<220> FEATURE:

```
<223> OTHER INFORMATION: PCR Primer

<400> SEQUENCE: 6
tttcacacag gcgtcataag ct                                                22

<210> SEQ ID NO 7
<211> LENGTH: 21
<212> TYPE: DNA
<213> ORGANISM: Artificial Sequence
<220> FEATURE:
<223> OTHER INFORMATION: PCR Primer

<400> SEQUENCE: 7
caagcttgct ggtgaaaagg a                                                 21

<210> SEQ ID NO 8
<211> LENGTH: 21
<212> TYPE: DNA
<213> ORGANISM: Artificial Sequence
<220> FEATURE:
<223> OTHER INFORMATION: PCR Primer

<400> SEQUENCE: 8
actaagcaga tggccacaga a                                                 21
```

METHODS OF INDUCING INDOLAMINE 2,3—DIOXYGENASE (IDO)

CROSS-REFERENCE TO RELATED APPLICATION

This application is a division of U.S. Ser. No. 13/997,356 filed Jun. 24, 2013, which is the U.S. national phase of PCT Application No. PCT/SE2011/051544 filed on Dec. 20, 2011, which claims priority to Swedish Patent Application No. 1051356-2 filed on Dec. 22, 2010, the disclosures of which are incorporated in their entirety by reference herein.

SEQUENCE LISTING

The text file titled Sequence_ST25.txt created Feb. 17, 2015, and of size 2 KB, filed herewith, includes a sequence listing and is hereby incorporated by reference.

Gene expression was demonstrated using Reverse Transcriptase-PCR (RT-PCR) using the kit (Superscript one-step RT-PCR with Platinum Taq, Invitrogen) according to the instructions. The sequences of forward primers and reverse primers for the human IDO-1 gene analyzed and the housekeeping gene HPRT respectively, were: IDO-1 forward: SEQ ID NO: 1—5'-GGCAAACTGGAAGAAAAAGG-3', reverse: SEQ ID NO: 2—5'-CAGACAAATATA TGC-GAAGAAC; HPRT Forward: SEQ ID NO: 3—5'-CAAGCTTGCTGGTGAAAAGGA-3', HPRT Reverse: SEQ ID NO: 4—5'-ACTAAGCAGATGGCCACAGAA-3'. The PCR conditions were set as follows: 1 denaturing cycle at 94° C. for 2 min followed by 40 cycles (for the IDO-1) or 30 cycles (for the HPRT) at 94° C. for 15 s, 53° C. for 30 s, and 72° C. for 30 s with a final extension reaction at 72° C. for 5 min.

FIELD OF INVENTION

The invention relates to the use of a composition comprising at least two compounds, each of which induces indolamine 2,3-dioxygenase, for the treatment of an autoimmune disorder or disease or immune rejection of transplants or gene therapeutically modified cells, wherein said inducers have different mechanism of action and wherein the composition gives rise to a synergistic effect on the IDO levels.

BACKGROUND OF INVENTION

Indoleamine dioxygenase (IDO) degrades the indole moiety of tryptophan and initiates the production of neuroactive and immunoregulatory metabolites, collectively known as kynurenines. The functional expression of IDO by dendritic cells has emerged in recent years as a major mechanism of peripheral tolerance. IDO contributes to maternal tolerance in pregnancy, control of allograft rejection, and protection against autoimmunity, inflammatory pathology and allergy. IDO expression also serves a physiological mechanism by which malignancies induce immune tolerance (Uyttenhove et al. 2004; Mellor et al. 2004; Munn et al. 2004). The wide spectrum of physiopathological conditions in which IDO appears at work suggests that this suppressive system is frequently involved in physiological down regulation of T cell responses and resulting inflammatory responses. There are a number of known substances that induces IDO, wherein said compounds have different mechanisms of action. Examples of classes of such IDO inducers, having different mechanisms of action, are among others cytidine analogues, histone deacetylase inhibitors, vitamin D3 analogues, interferons, toll like receptor ligands, gonadotropine receptor signalling hormones, prostaglandine E2 analogues, IDO stabilisers, soluble CTLA4 conjugates, and glycocorticoids.

However, many of these substances increase the amount of IDO to levels which are too low to be suitable in pharmaceutical composition, and will thus require, to induce effective IDO levels, high doses that are not suitable for reasons of toxicology, compliance or costs. Therefore there is a need to develop new pharmaceutical compositions that, at suitable dose levels, could increase IDO to levels that are sufficient and therapeutically useful in the treatment of different autoimmune disorders and in the prevention of transplant rejections.

SUMMARY OF THE INVENTION

The invention relates to the finding that compounds, that, when used alone, induces IDO to levels that are not sufficient in relation to the treatment regimes, could be used in mixtures or combinations of compounds that induce IDO, and that by mixing different IDO inducers having different mechanism of action, the increase in IDO was more than the sum of what each IDO inducer would have achieved alone, and in some cases up to 100 times larger than that additive effect. By making such a combination it will for the first time be possible to produce a pharmaceutical composition which could be used for the treatment of a mammal in need thereof for a number of diseases and disorders in which IDO induction is therapeutically useful.

In a first aspect the invention relates to a composition comprising at least two compounds, which induces IDO, for the treatment of an autoimmune disorder or disease or immune rejection of transplants or gene therapeutically modified cells, wherein said inducers have different mechanisms of action and give rise to a synergistic effect on the IDO level.

In a second aspect, the invention relates to a method of treating a mammal having an autoimmune disorder or disease or having an immune rejection of transplants or gene therapeutically modified cells, wherein the treatment induces IDO, comprising administering to a patient a therapeutically effective amount of the composition as defined above.

In a third aspect of the invention, dendritic cells or other antigen presenting cells, for example from peripheral blood or bone marrow of the patient or of another person, are cultured ex vivo in a suitable medium. To these cells are added the invented composition with the aim to induce IDO production and induce differentiation to cells that have an elevated IDO production. Simultaneously or soon thereafter, one or more antigens, that are associated with the condition being treated (e.g., an autoantigen responsible for an autoimmune disease) will be administered to the cells, whereafter the cells are transferred to the patient. This ex vivo treatment, or adoptive cell transfer as it may also be called in the scientific literature, will lead to a migration of the transferred cells to organs or tissues where they can activate T-cells to become suppressive T-cells or to become antigen-specific regulatory T-cells. The transferred cells can also migrate to sites of inflammation where they can locally perpetuate existing regulatory T-cells.

In a fourth aspect the invention relates to a method of inducing IDO in a cell culture comprising the steps of; providing isolated cells in a suitable medium, adding the composition as defined above, incubating said isolated cells with the composition and obtaining a cell culture in which IDO is induced.

BRIEF DESCRIPTION OF THE DRAWINGS

FIG. 2B: Synergistic effect on IDO expression by interferon gamma and valproic acid. Valproic acid at 0.5 mM.

FIG. 3: Synergistic effect on IDO expression by zebularine, interferon gamma and valproic acid. The result clearly demonstrates a synergistic effect of all the three substances on the IDO1 expression by THP-1 cells.

FIG. 4A: Synergistic effect on IDO expression by hCG and zebularine and by hCG and interferon gamma. Cells of the human monocytic cell line THP-1 were non-exposed (medium control), exposed to zebularine alone (100 uM), hCG alone (0, 1 units/ml), or a combination. The results of THP-1 cells exposed to the combination demonstrate a synergistic effect.

FIG. 4B: Results obtained when cells were non-exposed (medium control), exposed to hCG alone (0.01 units/ml), interferon gamma alone (200 IU/ml), or a combination. The THP-1 cells exposed to the combination demonstrated a synergistic effect.

FIG. 5: Kinetics of IDO 1 expression after exposure to interferon gamma for 24 hours from start and continuous exposure to zebularine. The aim of the study was to investigate the kinetics of interferon in combination with zebularine. The IDO1 induction by interferon gamma alone was strong after 24 hours but the effect was not sustained and dropped rapidly. In contrast, when combined with zebularine maintained for the whole period, the effect was sustained at days 2 and 3, although at a reduced level.

FIG. 16. Suppression of immunological rejection of allotransplanted pancreatic islets beneath the kidney capsule by daily intraperitoneal inoculations of zebularine for 14 days compared to untreated controls. Blood glucose follow up on zebularine treated rats as an indication of rejection. Figure shows treated animal results.

DETAILED DESCRIPTION OF THE INVENTION

Figure 1:
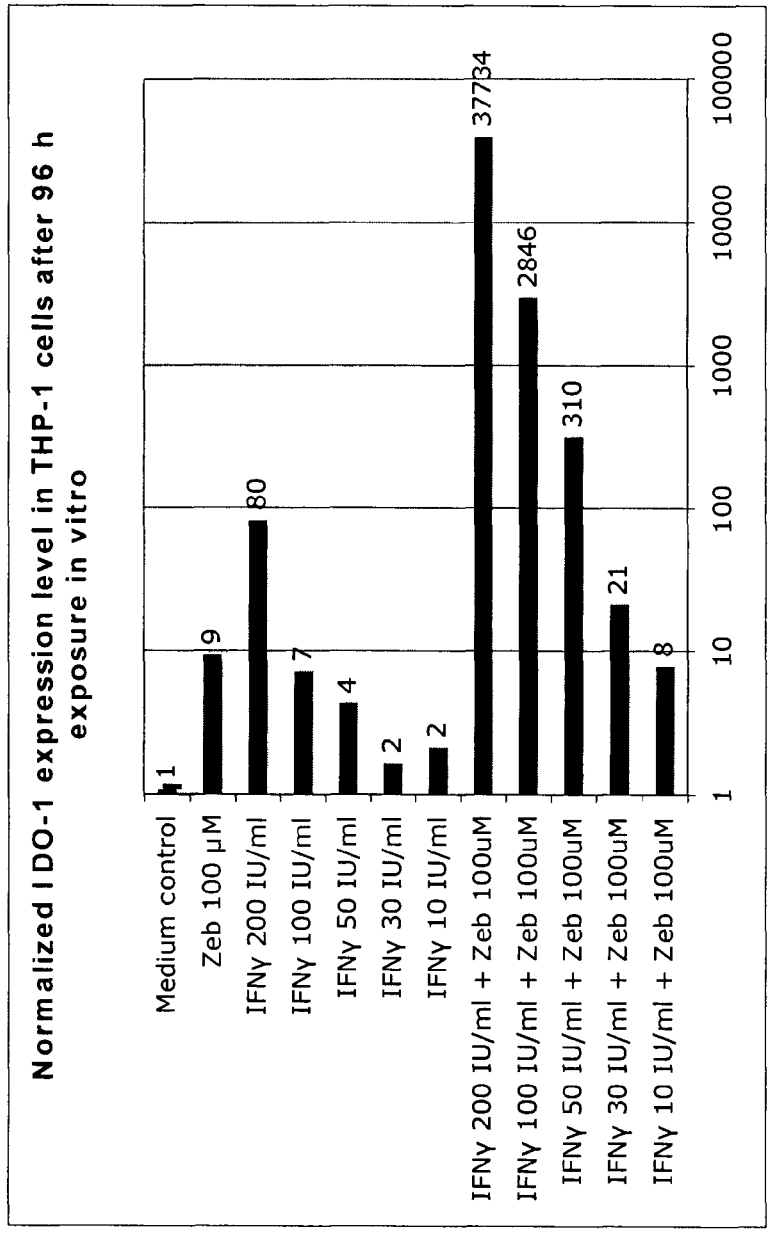
FIG. 1: Synergistic effect on IDO expression by zebularine and interferon gamma. The scale is logaritmic and the relative values are given for each bar.

In the context of the present application and invention, the following definitions apply:

The term "synergistic effect" is intended to mean an increase in the IDO levels, after the use of a combination of IDO inducers, that is significantly higher than the sum of the IDO levels achieved with each of the IDO inducers if used alone, said sum usually being referred to as an "additive effect".

The term "different mechanism of action" is defined as different ways to induce IDO, at the molecular level and/or by more complex biological pathways some of which may include immunological pathways. In particular, it is known from the literature that the different classes of IDO inducers shown in Table 1 below have wholly or partly different modes of actions regarding their IDO induction. These different classes are cytidine analogues, histon deacetylase inhibitors, vitamin D3 analogues, interferon gamma analogues, other interferons, such as interferon alpha, toll like receptor ligands, gonadotropine receptor signalling hormones, prostaglandine E2 analogues, IDO stabilizers, soluble CTLA4 conjugates, TGF-beta and glycocorticoids.

The term "immunosuppressive" is defined herein as an effect which reduces, arrests, or ameliorates immunological insult and is protective, resuscitative or revivative for affected tissue that has suffered cytotoxic insult from immune cells or inflammation.

The term "immunosuppressive agent" is herein defined as active ingredient or composition containing an immune insult treatment dose of active ingredient effective in reducing, preventing, arresting, or ameliorating immune insult and provides protection, resuscitation or revival to affected tissue that has suffered immune mediated insult or is in risk thereof.

The term "indolamine dioxygenase (IDO)" is intended to mean IDO-1 (indoleamine 2,3-dioxygenase, EC 1.13.11.52), or IDO-2 (indoleamine-pyrrole 2,3 dioxygenase-like 1, EC 1.13.11.-) that are two different proteins that can catabolize tryptophan. IDO-1 can also catabolize serotonin and melatonin but the substrate specificity for IDO-2 is not so well studied. Catabolites from the tryptophan pathway are Tryptophan, N-Formyl-kynurenine, Formylanthranilate, Anthranilate, L-Kynurenine, 4-(2-Aminophenyl)-2,4-dioxybutanoate, Kynurenic acid, 3-Hydroxy-L-kynurenine, 3-Hydroxyanthranilate, 3-Metoxy-anthranilate, 4-(2-Amino-3-hydroxy-phenyl)-2,4-dioxobutanoate, Xanthurenate, 8-Metoxy-kurenate, 2-Amino-3-carboxy-muconate semialdehyde, 2-Aminomuconate semialdehyde, Quimolinic acid, Cinnavalininate, Tryptamine, N-Methyltryptamine, Indoleacetate, 2-Formamino-benzoylacetate, 5-Hydroxy-L-tryptophan, 5-Hydroxy-N-formylkunerine, 5-Hydroxy-kunerine, 5-Hydroxy-kunerenamin, 4,6-Dihydroxy-quinoline, Serotonin, N-Acetyl-serotonin, Melatonin, 6-Hydroxy-melatonin, Formyl-N-acetyl-5-metoxykynurenamine, N-Methylserotonin, Formyl-5-hydroxy-kynurenamine, 5-Metoxytryptamine, 5-Hydroxyindole-acetaldehyde, 5-Hydroxyindoleacetate, 5-Metoxyindoleacetate, or 5-Hydroxyindole-acetylglycine to enhance the immunosuppressive IDO activity. Examples are Kynurenine, 3-hydroxy-kynurenine, anthranilic acid, 3-hydroxy-anthranilic acid, quinolinic acid and picolinic acid.

The immune suppression mediated by IDO is mediated by starvation of tryptophan, induction of apoptosis in lymphocytes and induction of regulatory T-cells (Treg). The apoptosis induction and Treg induction is mediated by the catabolites, why addition of such catabolites in combination with IDO induction by composition of the invention may enhance the clinical effect. The immune suppressive action from IDO may be explained by 1) starvation of tryptophan, 2) direct toxic effect from several of the above mentioned catabolites that induce apoptosis of immune cells, particularly L-Kynurenine, Anthranilate, 3-Hydroxy-anthranilate and 3-Hydroxy-L-kynurenine, and/or 3) that some of the catabolites stimulate the differentiation of T helper cells to immune suppressive regulatory T-cells important for tolerance.

An analogue is a molecule that differs in chemical structure from a parent compound, for example a homolog (differing by an increment in the chemical structure, such as a difference in the length of an alkyl chain), a molecular fragment, a structure that differs by one or more functional groups, a change in ionization. Structural analogues are often found using quantitative structure activity relationships (QSAR), with techniques such as those disclosed in Remington (The Science and Practice of Pharmacology, 19th Edition (1995), chapter 28).

The IDO gene expression is known to be induced in antigen presenting cells. Different IDO-producing subpopulations of dendritic cells or macrophages have a varying expression of the other enzymes in the tryptophan pathway and therefore can be anticipated to yield different subsets of catabolites. Dendritic cells (DC) and particularly the plasmacytoid dendritic cells (pDC) are the strongest mediators of IDO-dependent Tcell suppression (Fallarino et al., Current Drug Metabolism 8: 209-16, 2007).

IDO expression is subject to complex regulation by an array of signals, and the IDO levels may thus be induced or maintained by different mechanisms of actions. For example, IDO may be induced by inhibition of DNA methyl transferases or histone deacetylases which activates otherwise silenced promoters of IDO. IDO may also be induced by NFkB activation which results in IDO gene expression, said NFkB activation being induced by various factors such as interferon gammaR1/gamma R2 signaling, toll-like-receptor activation, etc. Furthermore, inhibitors of reactive oxidative species (ROS) may contribute to the stabilization of IDO, and so can other mechanisms that stabilize existing IDO levels or enhance the effects of existing IDO, or inhibit pathways that degrades or inactivates IDO. Another way to increase or maintain desired IDO levels is by inhibition of pathways that are downstream other IDO inducers but which do not lead to IDO induction, said inhibition thus favouring the IDO induction. Yet another mechanism is by activating interferon gamma, and/or other ways to activate an autocrine induction of IDO. These and other modes of action for IDO induction are described in Table 1.

The invention relates to a composition comprising at least two compounds, which induces IDO, for the treatment of an autoimmune disorder or disease or immune rejection of transplants or gene therapeutically modified cells, wherein said inducers have different mechanisms of action and give rise to a synergistic effect ("synergistic effect" being defined above) on the IDO level. Preferably, such synergistic effects should be significantly higher than the additive effect ("additive effect" being defined above), for example, at least three times higher. However, the synergistic effect is preferably more than three times higher, for example, 10, 20, 30, 40, 50 or 100 times higher, or even more such as shown in some of the in vitro examples presented below. Said inducers are selected from the group consisting of cytidine analogues, histon deacetylase inhibitors, vitamin D3 analogues, Interferon gamma analogues, other interferons, toll like receptor ligands, gonadotropine receptor signalling hormones, prostaglandine E2 analogues, IDO stabilizers, soluble CTLA4 conjugates, and glycocorticoids. Examples of different inducers are zebularine, valproic acid, human chorionic gonadotropine and interferon gamma. Other examples are those mentioned in Table 1 below.

The invented compositions may be used for the treatment of a disease selected from the group consisting of Achlorhydria, Acute hemorrhagic leukencephalitis, Addison's Disease, Alopecia Areata, Anemia, Pernicious Anti-Glomerular Basement Membrane Disease, Antiphospholipid Syndrome, Aplastic Anemia, Atopic Allergy, Autoimmune Atrophic Gastritis, Autoimmune Hearing Loss, Autoimmune hemolytic anemia, Autoimmune hypoparathyroidism, Autoimmune hypophysitis, Autoimmune Lymphoproliferative, Autoimmune Myocarditis, Autoimmune oophoritis, Autoimmune orchitis, Autoimmune Polyendocrinopathy-Candidiasis-Ectodermal-Dystrophy, Autoimmune Syndrome Type II, Polyglandular, Behcet Syndrome, Celiac Disease, Chagas Disease, Cholangitis, Sclerosing, Chronic Inflammatory Demyelinating Polyneuropathy, Chronic lymphocytic thyroiditis, Churg-Strauss Syndrome, Colitis, Ulcerative, Crohn's disease, Cryoglobulinemia, Cushing Syndrome, Dermatitis Herpetiformis, Dermatomyositis, Diabetes Mellitus (Insulin-Dependent), Diffuse Cerebral Sclerosis of Schilder, Encephalomyelitis, Autoimmune, Experimental (EAE), Epidermolysis Bullosa Acquisita, Erythematosis, Felty's Syndrome, Glomerulonephritis (IGA), Glomerulonephritis Membranous, Goodpasture Syndrome, Graves' Disease, Guillain-Barre Syndrome, Hamman-Rich syndrome, Hepatitis Autoimmune, Hepatitis Chronic Active, Idiopathic thrombocytopenia, Inflammatory Bowel Diseases, Insulin resistance—type B, Lambert-Eaton Myasthenic Syndrome, Lens-induced uveitis, Lichen Sclerosus et Atrophicus, Lupus Erythematosus Discoid, Lupus Erythematosus Systemic, Lupus Hepatitis, Lupus Nephritis, Lymphopenia, Meniere's Disease, Mixed Connective Tissue Disease, Mooren's ulcer, Mucocutaneous Lymph Node Syndrome, Multiple Sclerosis, Myasthenia Gravis, Myelitis Transverse, Myocarditis, Narcolepsy, Neuritis Autoimmune Experimental, Neuromyelitis Optica, Oculovestibuloauditory syndrome, Ophthalmia Sympathetic, Opsoclonus-Myoclonus Syndrome, Pancreatitis, Pemphigoid Bullous, Pemphigus foliaceous, Pemphigus Vulgaris, Polyarteritis Nodosa, Polychondritis Relapsing, Polyendocrinopathies Autoimmune, Polymyalgia Rheumatica, Polyradiculoneuropathy, Primary biliary cirrhosis, Psoriasis, Purpura Thrombocytopenic Idiopathic, Raynauds, Reiter Disease, Rheumatic Fever, Rheumatoid Arthritis, Sarcoidosis, Scleroderma, Sjogren's Syndrome, Spondylitis Ankylosing, Stiff-Person Syndrome, Still's Disease Adult Onset, Takayasu's Arteritis, Temporal Arteritis, Thyrotoxicosis, Type B Insulin Resistance, Uveomeningoencephalitic Syndrome, Wegener's Granulomatosis, Vitiligo. Specific examples of disearese includes Rheumatoid arthritis, Diabetes mellitus type I, Psoriasis, Sjogren's syndrome, Multiple Sclerosis, Crohn's disease, arteriosclerosis, Parkinson's disease, ALS (Amyotrophic lateral sclerosis) and dementiahe composition or in transplantations to inhibit immune rejection of organs, tissues, normal or gene therapeutically modified cells.

In particular, the invented compositions may be used for the treatment of Rheumatoid arthritis, Diabetes mellitus type I, Psoriasis, Sjogren's syndrome, Multiple Sclerosis, Crohn's disease, arteriosclerosis, Parkinson's disease, ALS (Amyotrophic lateral sclerosis) or dementia.

The invented composition may further comprise a pharmaceutically acceptable buffer, excipient, solvent or carrier.

"Pharmaceutically acceptable" means a non-toxic material that does not decrease the effectiveness of the biological activity of the active ingredients. Such pharmaceutically acceptable buffers, carriers or excipients are well-known in the art (see Remington's Pharmaceutical Sciences, 18th edition, A. R Gennaro, Ed., Mack Publishing Company (1990) and handbook of Pharmaceutical Excipients, 3rd edition, A. Kibbe, Ed., Pharmaceutical Press (2000).

The term "buffer" is intended to mean an aqueous solution containing an acid-base mixture with the purpose of stabilising pH. Examples of buffers are Trizma, Bicine, Tricine, MOPS, MOPSO, MOBS, Tris, Hepes, HEPBS, MES, phosphate, carbonate, acetate, citrate, glycolate, lactate, borate, ACES, ADA, tartrate, AMP, AMPD, AMPSO, BES, CABS, cacodylate, CHES, DIPSO, EPPS, ethanolamine, glycine, HEPPSO, imidazole, imidazolelactic acid, PIPES, SSC, SSPE, POPSO, TAPS, TABS, TAPSO and TES.

The term "solvent" is intended to mean an aqueous or non-aqueous liquid with the purpose of presenting, diluting and/or dissolving the composition. The solvent may be one or more of saline, water, polyethylene glycol, propylene glycol, ethanol or oils (such as safflower oil, corn oil, peanut oil, cottonseed oil or sesame oil).

The excipient may be one or more of carbohydrates, polymers, lipids and minerals. Examples of carbohydrates include lactose, sucrose, mannitol, and cyclodextrines, which are added to the composition, e.g. for facilitating lyophilisation. Examples of polymers are starch, cellulose ethers, cellulose carboxymethylcellulose, hydroxypropylmethyl cellulose, hydroxyethyl cellulose, ethylhydroxyethyl cellulose, alginates, carageenans, hyaluronic acid and derivatives thereof, polyacrylic acid, polysulphonate, polyethylenglycol/polyethylene oxide, polyethyleneoxide/polypropylene oxide copolymers, polyvinylalcohol/polyvinylacetate of different degree of hydrolysis, and polyvinylpyrrolidone, all of different molecular weight, which are added to the composition, e.g., for viscosity control, for achieving bioadhesion, for dilution, or for protecting the lipid from chemical and proteolytic degradation. Examples of lipids are fatty acids, phospholipids, mono-, di-, and triglycerides, ceramides, sphingolipids and glycolipids, all of different acyl chain length and saturation, egg lecithin, soy lecithin, hydrogenated egg and soy lecithin, which are added to the composition for reasons similar to those for polymers. Examples of minerals are talc, magnesium oxide, zinc oxide and titanium oxide, which are added to the composition to obtain benefits such as reduction of liquid accumulation or advantageous pigment properties.

The composition may be administered to a mammal in need thereof in a suitable amount to achieve an effect corresponding to such concentrations that induce a strong IDO activity in vitro of said at least two inducers.

By having a direct effect on the immune system, treatment with a suitable dose it is also possible to use the composition for pretreatment of transplants (organs, tissues or cells) by inducing IDO expression in the endothelial cells and as a consequence making them less immunogenic to the host and reducing the risk of rejection of the grafted cells. By subsequent treatment of the graft recipients with the composition, at a dose providing immune suppression in vivo, a permanent survival of the transplants can be achieved without further immunosuppressive therapy or with minimal such therapy.

To treat a patient, the invented composition may be administered at dose levels that will achieve concentrations in vivo, at the sites or locations of action, that become between 5 µM to 10 mM, or other lower or higher levels that are effective, depending on which disease or disorder to be treated and on which IDO-inducer is referred to. For IDO-inducers for which concentrations are normally not expressed as molar concentrations (M), other numerical values apply, for example 0.001 IU/mL to 100 MIU/mL, or more narrow ranges such as 1-1000 IU/mL, or other suitable levels. Similarly, other numerical values apply when the resulting levels are expressed as ng/mL, mg/mL, mg/kg body weight, etc. Initially, a higher dose may be used such as followed by a lower maintaining dose. For the ex vivo treatment (adoptive cell transfer), similar concentrations as those outlined above should be achieved albeit these are in vitro/ex vivo concentrations and not in vivo concentrations. The doses aimed for, for each IDO-inducers, will also be dependent upon which other synergistically acting IDO inducer(s) that is used. Furthermore, as the number of IDO-inducers in the invented and synergistically acting composition can be two, three, four or more, it is obvious that a very large number of feasible dose levels can be defined.

The invented composition may be administered by any suitable route including oral, sublingual, buccal, nasal, inhalation, parenteral (including intraperitoneal, intraorgan, subcutaneous, intradermal, intramuscular, intra-articular, venous (central, hepatic or peripheral), lymphatic, cardiac, arterial, including selective or superselective cerebral arterial approach, retrograde perfusion through cerebral venous system, via catheter into the brain parenchyma or ventricles), direct exposure or under pressure onto or through the brain or spinal tissue, or any of the cerebrospinal fluid ventricles, injections into the subarachnoid, brain cisternal, subdural or epidural spaces, via brain cisterns or lumbar puncture, intra and periocular instillation including application by injection around the eye, within the eyeball, its structures and layers, the ear, including the Eustachian tube, mastoid air cells, external and internal auditory canals, tympanic membrane, middle ear, inner ear including the cochlear spiral ganglion and labyrinthine organs, as well as via enteral, bowel, rectal, vaginal, urethral or bladder cisternal. Also, for in utero and perinatal indications, then injections into the maternal vasculature, or through or into maternal organs including the uterus, cervix and vagina, and into embryo, foetus, neonate and allied tissues and spaces such as the amniotic sac, the umbilical cord, the umbilical artery or veins and the placenta, may be used. The preferred route may vary depending on the condition of the patient and the composition used in each case.

The effect of the invented composition may be combined with an immunosuppressive agent to reduce the frequency of effector immune cells during or before the induction of tolerance.

This invention includes the possibility of using the timing and sequence of delivery of the invented composition to induce tolerance in an optimal way. It also includes the possibility of using the timing and sequence of delivery of the individual IDO inducers, that comprises the invented composition, to induce tolerance in an optimal way. For example, when the invented composition comprise two IDO inducers ("A" and "B"), A may be administered first, by a certain administration route and dosage regime (dose, concentrations, frequency, etc.). Thereafter, B will be administered at another route, dose and dosage regime. Finally, one of A or B can be stopped before the other. A large number of such different and synergistic treatment regimes can be envisioned for the various combinations invented, each one taking into consideration each IDO inducer's IDO inducing efficacy, gene expression kinetics, pharmacokinetics, etc.

The composition may comprise additional active ingredients such as methotrexate, rapamycin, cyclophosphamide, antimetabolites including azathioprine, inhibitors of nucleotide synthesis (including mycophenolate mofetil, mizoribine, leflunomide, FK778), FTY720, lymphocyte depleting antibodies (including polyclonal antibodies to lymphocytes, thymocytes, T-cells, muromonab-CD3, rituximab, alemtuzumab, CAMPATH-1), non-depleting antibodies (daclizumab etc., LFA3-Ig fusion protein), anti-TNF antibodies (including infliximab, adalimumab), natalizumab (anti-VLA-4), the anti-CD 154 antibodies BG9588 and IDEC 131), soluble cytokine receptors (including lenercept and etanercept (soluble TNF p55 and TNF p75 receptors), and anakinra (soluble IL-IRA). The immunosuppressive drugs mentioned above can be used in combination with the composition of the invention to reduce the number of immune effector cells.

The composition may be distributed and made available in convenient unit dosage forms such as capsules and ampoules and may be manufactured and distributed by any of the methods known to the pharmaceutical arts. In addition to the active ingredient, the composition can also contain other usual agents of the art relating to the type of composition produced. This may, by example, take the configuration of suspensions, solutions and emulsions of the active ingredient in lipid, non-aqueous or aqueous diluents, solvents, dissolving agents, emulsifiers, syrups, granulates or powders, or mixtures of these. The composition can also contain colouring agents, preservatives, perfumes, flavouring additions and sweetening agents. In addition to the active ingredient, the composition can also contain other pharmaceutically active medications. The manufacture and distribution of the composition is carried out by techniques known to the art, such as, evenly and intimately bringing together the active ingredient with liquids or fine solids or both, and then if needed, forming the composition into a dose unit form. The discrete dose, portion and carrier vehicle constituting the composition will generally be adapted by virtue of shape or packaging for medical administration and distributed for this purpose.

Tablets can be manufactured and distributed by compression or mould, from active ingredient possibly with one or more additional pharmaceutically active compounds. Compressed tablets can be manufactured and distributed through compression in a machine typical to the art a known quantity of the active ingredient in a dispersible configuration such as powder or granules, possibly mixed with other agents including binders, lubricants, inert diluents, preservatives, and dispersing agents. Moulded tablets can be manufactured and distributed by moulding in a machine typical to the art a mix of known quantity of active ingredient addition pharmaceutically active compounds and other additives moistened with a liquid diluent. The tablets can possibly be coated, enveloped or covered, with substances including protective matrices, which can contain opacifiers or sweeteners and can be formulated to allow slow or controlled release, or also release within a certain part of the digestive system of the contained active ingredients. Capsules can be manufactured and distributed by placement of a known quantity of active ingredient, additional pharmaceutically active compounds and additives within a two part or sealed capsule of gelatine or other aqueous dissolvable substance. The active ingredient can also be manufactured and distributed as a composition in microencapsulated, microsomal, micellar and microemulsion forms.

The compositions containing the active ingredients acceptable for oral topical administration can be manufactured and distributed as lozenges containing the active ingredients, other pharmaceutically active compounds, and additives in a flavoured basis, such as *acacia* and tragacanth; as pastilles containing the active ingredient with other pharmaceutically active compounds, and additives in an inert base such as gelatine and sucrose: as mouthwashes or rinses containing the active ingredient with other pharmaceutically active compounds, and additives in an acceptable liquid.

The composition containing the active ingredient acceptable for skin topical administration can be manufactured and distributed as ointments, oils, creams, lotions, gels, pastes and as transdermal patches containing the active ingredient, other pharmaceutically active compounds, additives and an acceptable carrier medium.

The compositions containing the active ingredient acceptable for nasal administration can be manufactured and distributed with other pharmaceutically active compounds and additives as a powder for inhalation, or as an oily, aqueous or non-aqueous liquid for nasal spray or drops.

The compositions containing the active ingredient acceptable for rectal administration can be manufactured and distributed as suppositories, creams, foams, douches or enemas with other pharmaceutically active compounds, suitable bases of the usual water-soluble diluents, fats, and additives known to practitioners of the art.

The composition containing the active ingredient acceptable for vaginal administration can be manufactured and distributed as pessaries, suppositories, creams, gels, foams, douches or sprays with other pharmaceutically active compounds, suitable bases and additives known to practitioners of the art.

The composition containing the active ingredient acceptable for parenteral administration can be manufactured and distributed from aqueous and non-aqueous sterile injection solutions, other pharmaceutically active compounds, additives including anti-oxidants, bacteriostats and solutes and sugars such as mannitol to make the composition isotonic, hypotonic or hypertonic with the blood of the recipient; and also aqueous and non-aqueous sterile suspensions which can include suspenders and thickeners. The composition can be manufactured and distributed in unit-dose or multi-dose containers, such as sealed glass or plastic ampoules, vials, bottles and bags as a liquid, and in a dry state requiring only the addition of sterile liquid, for example water, saline or dextrose solutions, immediately prior to use. Extemporaneous solutions and suspensions for injection can be prepared from powders and tablets of the kind above described.

The composition containing the active ingredient acceptable for administration into the brain and related structures, spinal cord and related structures, ventricular system and cerebrospinal fluid spaces can be manufactured and distributed as aqueous and non-aqueous sterile injection solutions, containing other pharmaceutically active compounds, additives including anti-oxidants, bacteriostats and solutes and sugars such as mannitol to make the composition isotonic, hypotonic or hypertonic with the cerebrospinal fluid; and also aqueous and non-aqueous sterile suspensions which can include suspenders and thickeners. The composition can be manufactured and distributed in unit-dose or multi-dose containers, such as sealed glass or plastic ampoules, vials, bottles and bags as a liquid, and in a dry state requiring only the addition of sterile liquid, for example water, saline or dextrose solutions, immediately prior to use. Extemporaneous solutions and suspensions for injection can be prepared from powders and tablets of the kind above described.

The desired unit dose of compositions, are those containing a daily dose or immune insult treatment dose or an appropriate fraction thereof, of the administered active ingredient. Unit dose forms of the invention may also include more complex systems such as double barreled syringes, syringes with sequential compartments one of which may contain the active ingredient, and the other any necessary diluents or vehicles. The agents in the syringes would be released sequentially or as a mixture or combination of the two after the triggering of the syringe plunger. Such systems are known in the art.

The composition may be used for the treatment of a disease or disorder such as those mentioned above.

TABLE 1

Eleven classes of IDO-inducing substances

| Class | Examples of substances in the class | Other substances in the class | Mechanism-of-Action for the IDO induction |
|---|---|---|---|
| Cytidine analogues | Zebularine, deoxy-azacytidine, aza-cytidine | Other zebularine derivatives and cytidine analogues 5-methylcytidine, 2'-deoxyzebularine, 5-fluoro-zebularine, 5-fluoro-2'-dexyzebularine, 5-chloro-zebularine, 5-chloro-2'-dexyzebularine, 5-bromo-zebularine, 5-bromo-2'-dexyzebularine, 5-iodo-zebularine, 5-iodo-2'-dexyzebularine, 5-methylpyrimidin-2-one, 5-Me-2'-deoxyzebularine, or mono, di- or triphosphates thereof | DNA methyl transferase inhibition, activating the otherwise silenced promoters of IDO-1, and possibly of FoxP3 and interferon gamma |
| Histone deacetylase inhibitors | Valproic acid, trichostatin A, vorinostate (SAHA) | Other hydroxamic acids, cyclic tetrapeptides (trapoxin B) and depsipeptide, benzamides, electrophilic ketones, phenylbutyrate, belinostate (PXD 1010), LAQ824, panobinostat (LBH589), CI994, mocetinostate (MGCD0103) | Histon deacetylase inhibition, activating the otherwise silenced promoters of IDO-1 and possibly of FoxP3 and interferon gamma |
| Vitamin D3 analogues | Calcitriol (1,25(OH)$_2$D$_3$) | Dihydrotakysterol, alphacalcidol, calcitriol, paricalcitol | 1,25(OH)$_2$D$_3$ inhibits Th1 (IL2, IFNg) and Th17 and inhibits IL 12 production, all of which takes place at least partially via IDO induction |
| Interferon gamma analogues* | Interferon gamma | Interferon gamma analogues, IFN-g inducers (IL12, IL18, 4-IBB mAb) | Interferon gammaR1/gammaR2 signaling induced NFkB activation which results in IDO gene expression |
| Other interferons | Interferon A, interferon B1, interferon-tau | Interferon W1, interferon K, | Interferon receptor induced NFkB activation which results in IDO gene expression |

TABLE 1-continued

Eleven classes of IDO-inducing substances

| Class | Examples of substances in the class | Other substances in the class | Mechanism-of-Action for the IDO induction |
|---|---|---|---|
| Toll like receptor (TLR) ligands | CpGcontaining DNA oligonucleotides (e.g., ODN 1826 & 2006), lipopoly-saccharides | Other unmethylated CpG motifs, double stranded RNA, single stranded RNA, double-stranded unmethylated CpG-rich DNA. | TLR-activated NFkB activation resulting in IDO gene expression |
| Gonadotropine receptor signaling hormones | Recombinant human chorionic gonadotropine (rhCG), prolactin | Luteinizing hormone (LH) | Gonadotropine-receptor signaling, resulting in IDO gene expression |
| Prostaglandins E2 analogues | Prostaglandin E2 (PGE2) | Other prostaglandins E2 analogues, e.g., ®-15-methyl PGE2 methyl ester, (S)-15 methyl PGE2 methyl ester, or 16-dimethyl PGE2 | PGE2-receptor signaling, resulting in IDO gene expression |
| IDO stabilizers | TGF-beta, iInterleukin-10 | TGF-beta 1:2, 1:33 and 2:3, GDNF, BMPs | Inhibitors of Reactive Oxidative Species (ROS), thereby stabilizing IDO. As well as other IDO stabilizing or IDO effect enhancing mechanisms |
| Soluble CTLA4 conjugates | CTLA4-1g (abatacept/Orencia ®) | Other soluble CTLA4 conjugates | Binding to CD80/86 activating interferon gamma, with an autocrine induction of IDO |
| Glycocorticoids | Dexamethasone | Other glycocorticoid analogues | Industion of GITR ligand in dendritic cells and upregulation of GITR in T cells enhance the reverse signaling in DC trough GITRL inducing IDO expression |

Following examples are intended to illustrate, but not to limit, the invention in any manner, shape, or form, either explicitly or implicitly.

EXAMPLES

Example 1. Synergistic Effect on IDO Expression by Zebularine and Interferon Gamma Materials and Methods THP-1 (ATCC: TIB-202) is a human monocytic cell line that originates from an acute monocytic leukemia. It has the phenotype of monocytes but can be differentiated to a more dendritic phenotype. In the current study, the THP-1 cells were in vitro passaged in RPMI 1640 medium supplemented with 5% or 10% FCS, 10 mM Hepes, 1 mM Sodium pyruvate, and 50 ug/ml gentamicin (R5 or R10 medium respectively). The cell density was adjusted to 200 000 cells per ml, and the cultures were incubated for four to seven days at 37° C. with 10% $CO_2$ in a humidified incubator. The substance, or combination of substances, being studied, were added to the medium at specified time points and in the case of IFN-gamma removed from medium as indicated. 96-168 hours after initiation of treatment, the IDO expression was assessed by PCR or by Quantitative PCR (Roche). RNA was extracted from cells cultured in flasks or six-well plates using Trizol reagent according to Invitrogen's protocol. Residual DNA was removed through Rnase free DNase (Roche Applied Science) treatment. Quality and quantity of the isolated RNA was measured by spectrophotometer and gel electrophoresis.

Gene expression was demonstrated using Reverse Transcriptase-PCR (RT-PCR) using the kit (Superscript one-step RT-PCR with Platinum Taq, Invitrogen) according to the instructions. The sequences of forward primers and reverse primers for the human IDO-1 gene analyzed and the housekeeping gene HPRT respectively, were: IDO-1 forward: 5'-GGCAAACTGGAAGAAAAAGG-3', reverse: 5'-C AGAC AAAT AT A TGCGAAGAAC; HPRT Forward: 5'-CAAGCTTGCTGGTGAAAAGGA-3', HPRT Reverse: 5'-ACTAAGCAGATGGCCAC AGAA-3'. The PCR conditions were set as follows: 1 denaturing cycle at 94° C. for 2 min followed by 40 cycles (for the IDO-1) or 30 cycles (for the HPRT) at 94° C. for 15 s, 53° C. for 30 s, and 72° C. for 30 s with a final extension reaction at 72° C. for 5 min.

Quantitative real-time PCR analyses (qRT-PCR) were performed using Super-Script III Platinum Two-Step qRT-PCR Kit with SYBR Green (Invitrogen). A total of 100-500 ng total RNA was used in a 20 ul RT reaction using a mixture of polydT and random hexamer primers. The cDNA obtained was diluted to a total volume of 80 ul and stored at −20° C. The primer sequences for the different genes were designed using Gene Fisher software support (G. Giegerich, F. Meyer, C. Schleiermacher, ISMB-96). The primers used for amplification of the IDO gene were: Forward: SEQ ID NO: 5—5'-AGTCCGTGAGTTTGTCCTTTCAA-3', Primer sequences, Reverse: SEQ ID NO: 6—TTTCACA-CAG-GCGTCATAAGCT-3'.

Hypoxanthine guanine phosphoribosyl transferase (HPRT) HPRT Forward: SEQ ID NO: 7—5'-CAAGCTT-GCTGGTGAAAAGGA-3', HPRT Reverse: SEQ ID NO: 8—5'-ACTAAGCAGATGGCCACAGAA-3' according to the cDNA sequence, were used. The qRT-PCR was performed in 20 ul reaction consisting of 2 ul diluted cDNA (12.5 ng), 0.3 uM of each primer, 1 ul bovine serum albumin (50 ug/ml), and 10 ul Platinum SYBR Green qRT-PCR superMix-UDG. The amplification of IDO was carried out in a Light Cycler (Roche Molecular Biochemicals) with the following thermal profile: Platinum SYBR Green qRT-PCR superMix-UDG incubation at 50° C. for 2 min, then denaturing at 95° C. for 5 min, followed by 45 cycles at 94° C. for 2 s, 58° C. for 10 s, and 72° C. for 14 s. The amplification of HPRT was carried out as follows, UDG incubation at 50° C. for 2 min, denaturing at 95° C. for 5 min, followed by 45 cycles at 94° C. for 2 s, 55° C. for 10 s, and 72° C. for 14 s. After amplification a melting curve analysis was performed. The qRT-PCR experiments were always run in triplicate.

Results and Discussion

Cells of the human monocytic cell line THP-1 were non-exposed (medium control), or exposed to zebularine (Berry & Associates, Inc. USA) alone, or to interferon gamma IFNg, Sigma) alone at different concentrations (FIG. 1). The cells were also exposed to 100 uM of zebularine in combination with various concentrations of interferon gamma. The scale is logaritmic and the relative values are given for each bar. It is striking that e.g., zebularine alone at 100 uM gave a value of 9 and 200 IU/ml of interferon gamma gave a value of 80. The sum of these values is 89, whereas when both are given together the IDO1 expression reached a value above 37 000. This demonstrates the synergistic induction of IDO1 expression in THP-1 cells by the two substances.

Figure 2A:
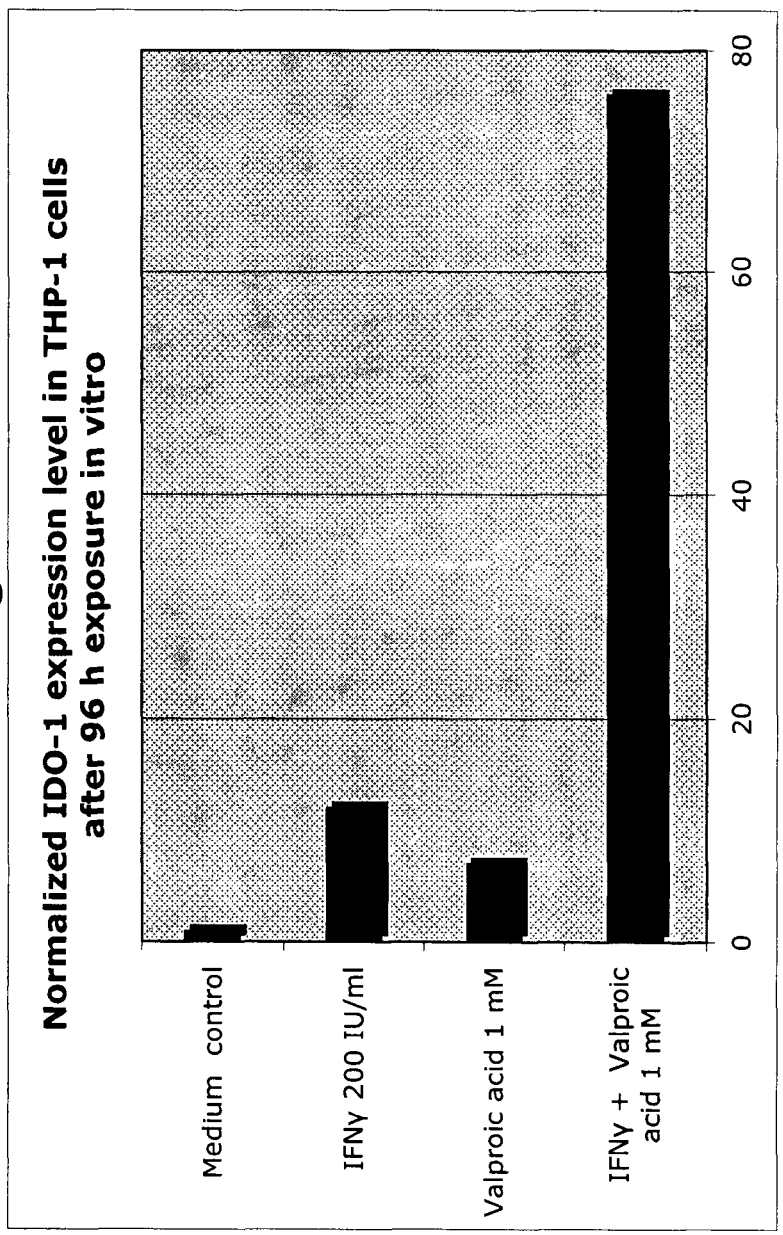
FIG. 2A: Synergistic effect on IDO expression by interferon gamma and valproic acid. Valproic acid at 1 mM.

Example 2. Synergistic Effect on IDO Expression by Interferon Gamma and Valproic Acid Materials and methods used were the same as described in Example 1 above. Cells of the human monocytic cell line THP-1 were non-exposed (medium control), exposed to interferon gamma alone (200 IU/ml), valproic acid (Sigma) alone (1 mM) or to the combination (FIG. 2A). The results of THP-1 cells exposed to the combination demonstrate a synergistic effect. Similar experiments but with the valproic acid concentration reduced to 0.5 mM was also performed (FIG. 2B). A synergistic effect on IDO1 expression was demonstrated also with this combination.

Example 3. Synergistic Effect on IDO Expression by Zebularine, Interferon Gamma and Valproic Acid Materials and methods used were the same as described in Example 1 above. Cells of the human monocytic cell line THP-1 were non-exposed (medium control), exposed to zebularine alone (100 uM), to interferon gamma alone (200 IU/ml) or valproic acid alone (1 mM) (FIG. 3). The THP-1 cells were exposed to the three substances pairwise and also with all three substances in combination. The scale is logaritmic and the relative values are given for each bar. The result clearly demonstrates a synergistic effect of all the three substances on the IDO1 expression in THP-1 cells.

Example 4. Synergistic Effect on IDO Expression by Human Chorionic Gonadotropine (hCG) and Zebularine, and by hCG and Interferon Gamma Materials and methods used were the same as described in Example 1 above. Cells of the human monocytic cell line THP-1 were non-exposed (medium control), exposed to zebularine alone (100 uM), hCG (Pregnyl, Sweden) alone (0.1 units/ml), or a combination (FIG. 4A). The results of THP-1 cells exposed to the combination demonstrate a synergistic effect. FIG. 4B shows results when cells were non-exposed (medium control), exposed to hCG alone (0.01 units/ml), interferon gamma alone (200 IU/ml), or a combination. The combination demonstrates a synergistic effect on IDO1 expression in THP-1 cells.

Example 5. Kinetics of IDOL Expression after Exposure to Interferon Gamma for 24 Hours from Start and Continuous Exposure to Zebularine Materials and methods used were the same as described in Example 1 above. Cells of the human monocytic cell line THP-1 were exposed to zebularine alone (100 uM), interferon gamma (200 IU/ml) alone or the two substances in combination (FIG. 5). The aim of the study was to investigate the kinetics of interferon in combination with zebularine. The THP-1 cells were divided into four groups, one exposed to interferon gamma alone for 24 hours, another to zebularine alone for the entire incubation period, and a third group exposed to interferon gamma for the initial 24 hours in combination with zebularine for the entire incubation period. The THP-1 cells were washed after 24 hours and zebularine was replaced. The four groups of THP-1 cells were harvested for RNA isolation after 24, 48, 72 or 96 hours. The 24 hours exposure to zebularine alone gave no IDO1 induction. After 96 hours a small increase in IDO1 induction by zebularine was detected. The IDO1 induction by interferon gamma alone was strong after 24 hours but the effect was not sustained and dropped rapidly. In contrast, when combined with zebularine maintained for the whole period, the effect was sustained at days 2 and 3, although at a reduced level.

Figure 6:
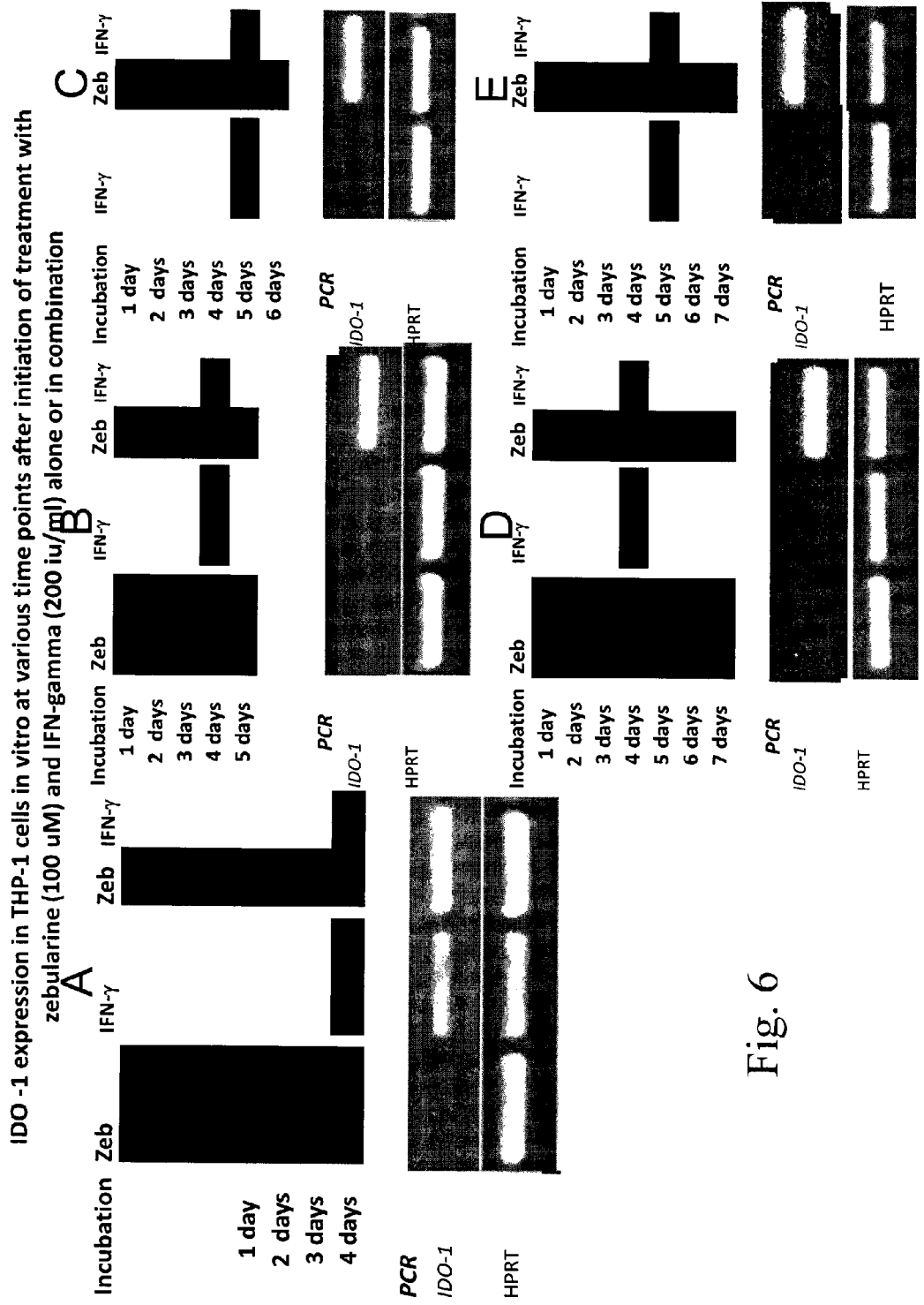
FIG. 6: Kinetics of IDO 1 expression after interferon gamma exposure for 24 hours after different pre-exposure times to zebularine. Kinetics of synergistic effect on IDO expression by zebularine and interferon gamma. In panel A we demonstrate a low effect of zebularine after four days. Interferon gamma alone given after 3 days, 24 hours before harvest gives a strong band and when interferon gamma is added after 3 days, 24 hours before harvest of THP-1 cells exposed to zebularine, it gives a stronger effect, demonstrating a synergistic effect also when zebularine preceeds the interferon with 3 days. In panel B, the THP-1 cells were given zebularine alone during 5 days and a weak band was detected. Interferon gamma alone given after 3 days and washed away 24 hours later, showed a weak band when tested 24 hours after removal of interferon. This is in agreement with results presented in FIG. 5. The combination of zebularine from start and interferon gamma given for 24 hours after three days, resulted in a sustained high expression level. In panel C the THP-1 cells were exposed to zebularine for 6 days and interferon gamma was given during 24 hours after four days and the cells were harvested after a total of 6 days. Again almost no IDO1 induction by interferon gamma alone was detected, but with the combination a strong IDO1 expression was observed. In panel D and E the THP-1 cells were exposed to zebularine for 7 days and to interferon gamma for 24 hours, either after three days (panel D) or after four days (panel E). A sustained strong IDO1 expression by the combination is illustrated in both panel D and E.

Example 6. Kinetics of IDOL Expression after Interferon Gamma Exposure for 24 Hours after Different Pre-Exposure Times to Zebularine Materials and methods used were the same as described in Example 1 above. FIG. 6 demonstrates the kinetics of synergistic effect on IDO expression by zebularine and interferon gamma. In panel A we demonstrate by reverse transcriptase PCR (RT-PCR) a low effect of zebularine after four days. Interferon gamma alone given after 3 days, 24 hours before harvest gives a strong band and when interferon gamma is added after 3 days, 24 hours before harvest of THP-1 cells exposed to zebularine, it gives a stronger effect, demonstrating a synergistic effect also when zebularine preceeds the interferon with 3 days. In panel B, the THP-1 cells were given zebularine alone during 5 days and a weak band was detected. Interferon gamma alone given after 3 days and washed away 24 hours later, showed a weak band when tested 24 hours after removal of interferon. This is in agreement with results presented in FIG. 5. The combination of zebularine from start and interferon gamma given for 24 hours after three days, resulted in a sustained high expression level. In panel C the THP-1 cells were exposed to zebularine for 6 days and interferon gamma was given during 24 hours after four days and the cells were harvested after a total of 6 days. Again almost no IDO1 induction by interferon gamma alone was detected, but with the combination a strong IDO1 expression was observed. In panel D and E the THP-1 cells were exposed to zebularine for 7 days and to interferon gamma for 24 hours, either after three days (panel D) or after four days (panel E). A sustained strong IDO1 expression by the combination is illustrated in both panel D and E. As an RNA control we have used HPRT.

Example 7. Synergistic Effect on IDO Expression by Zebularine and Interferon A

Figure 7:
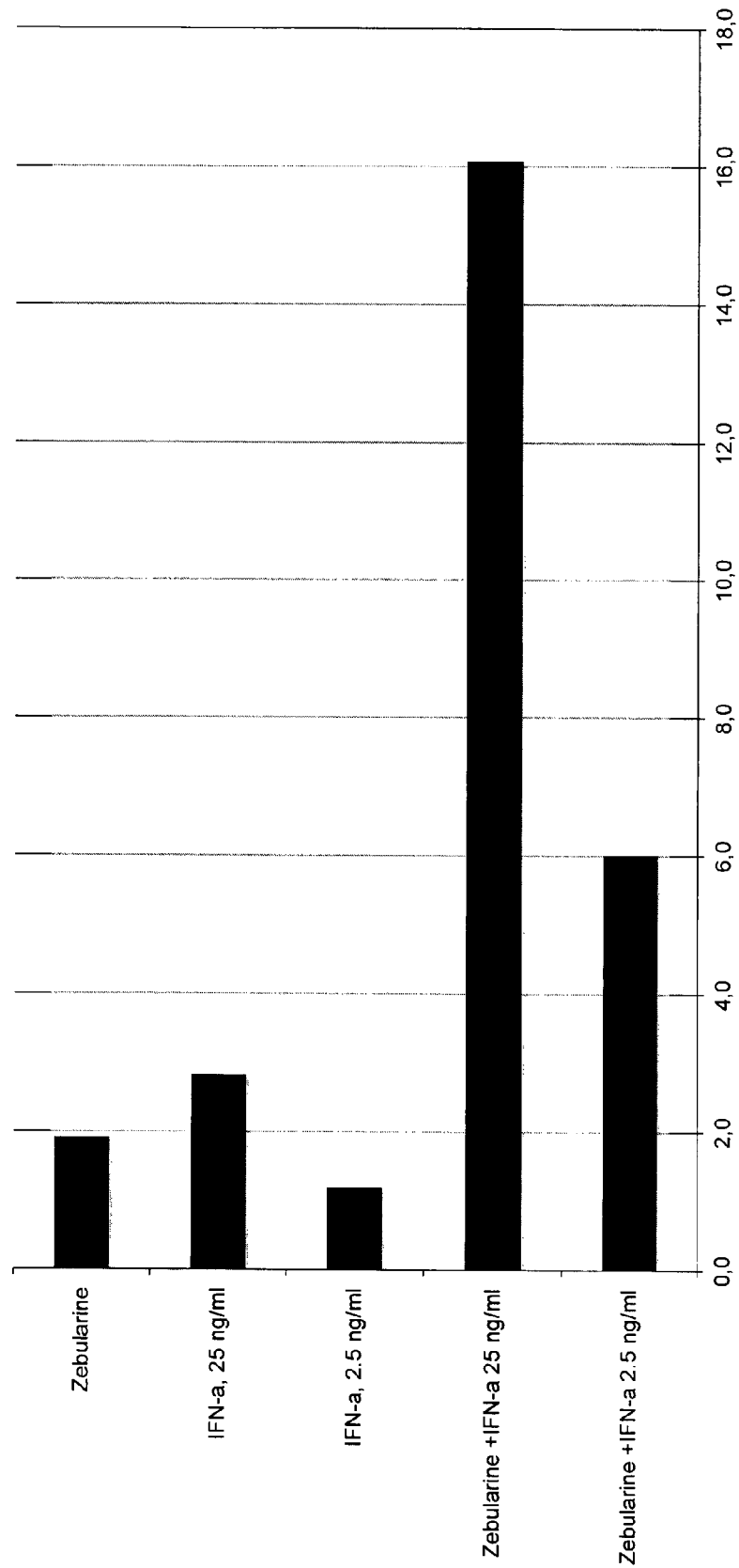
FIG. 7: Synergistic effect on IDO expression by zebularine and two concentrations of interferon A, 2.5 and 25 ng/ml, respectively FIG. 8. Synergistic effect on IDO expression by zebularine, interferon gamma and interferon A FIG. 9. Synergistic effect on IDO expression by zebularine, interferon gamma and TGF-b1

Materials and methods used were the same as described in Example 1 above. Cells of the human monocytic cell line THP-1 were non-exposed (medium control), exposed to 100 uM zebularine (Berry & Associates, Inc. USA) alone, or to interferon A (interferon alpha, "IFN-A", Sigma) alone at two different concentrations, 2.5 and 25 ng/ml (FIG. 7). The cells were also exposed to 100 uM of zebularine in combination with IFN-A at the same two concentrations. Zebularine was present during the entire incubation, whereas IFN-A was added after 96 h and RNA isolated after 120 h. The sum of the IDO1 expressions induced by zebularine alone and IFN-A alone is 3.1 and 4.7, respectively, for the lower and higher doses of IFN-a, but for combined treatment 6.0 and 16.1 at the two IFN-A dose levels. This demonstrates the synergistic induction of IDO1 expression by the two substances.

Figure 8:
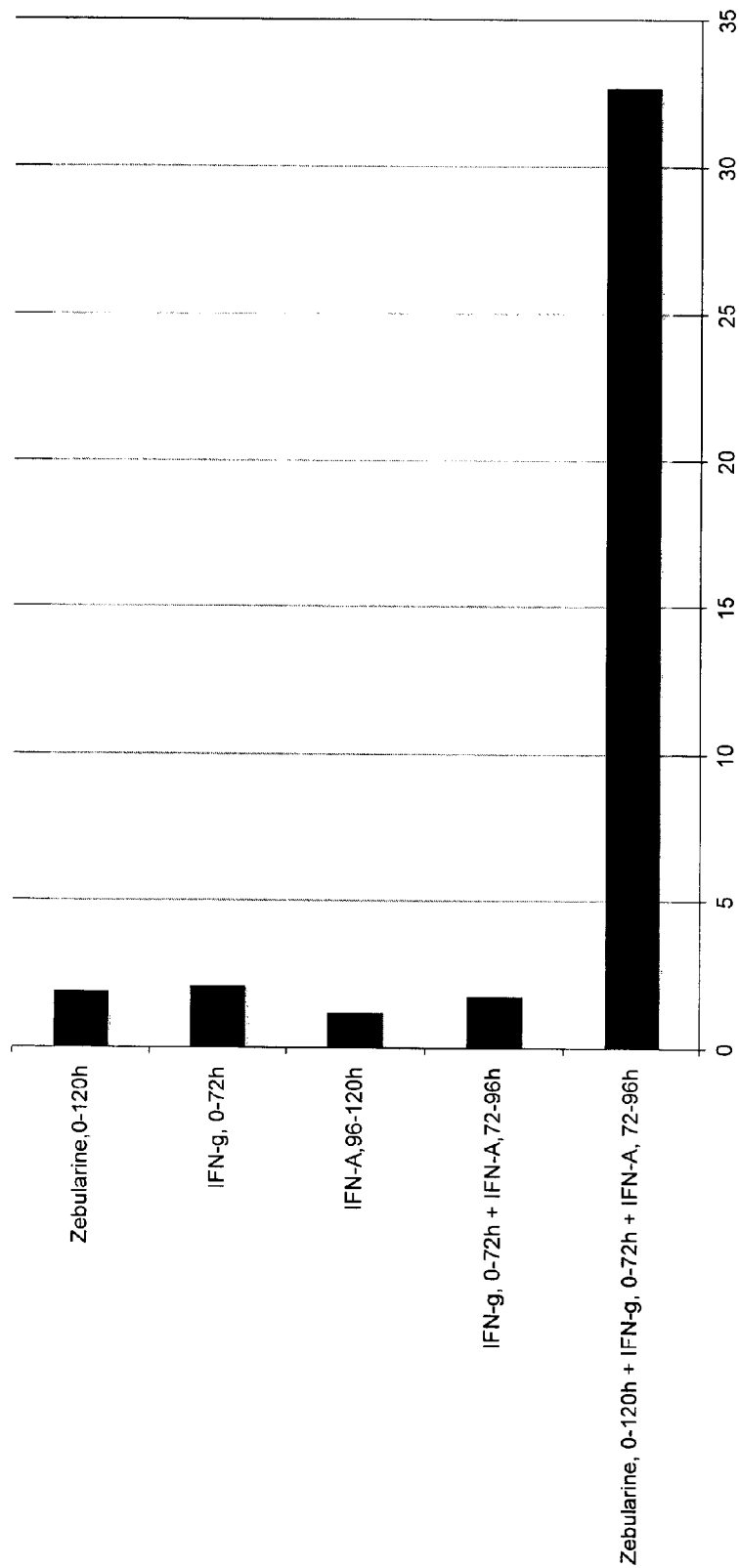

Example 8. Synergistic Effect on IDO Expression by Zebularine, Interferon Gamma and Interferon A Materials and methods used were the same as described in Example 1 above. Cells of the human monocytic cell line THP-1 were non-exposed (medium control), exposed to 100 uM zebularine (Berry & Associates, Inc. USA) alone, or to 2.5 ng/ml interferon alpha (IFN-A, Sigma) alone, or to 50 iu/ml interferon gamma (IFN-g) alone, and to both IFN-g and IFN-A, or finally to a combination of all the three substances (FIG. 8). Combined treatment with IFN-g and IFN-A was performed by adding IFN-g to medium at time 0 and replacing this medium at time 72 h by medium containing IFN-A, and at time 96 h replacing this medium with medium without additives. Treatment with a combination of all three substances was performed by including zebularine and IFN-g in medium in the interval 0-72 h, then replacing it with medium containing IFN-A and zebularine, and after another 24 h this medium was replaced with medium containing zebularine alone. The treatments with singular substances were performed in the same intervals, and at the end of the interval the medium was replaced with medium without additives. The combination of all three substances induces a strong synergistic effect on IDO1 expression. The strong synergistic effect is observed 48 h after removal of IFN-g and 24 h after removal of IFN-A, indicating a sustained synergistic effect on IDO1 expression.

Figure 9:
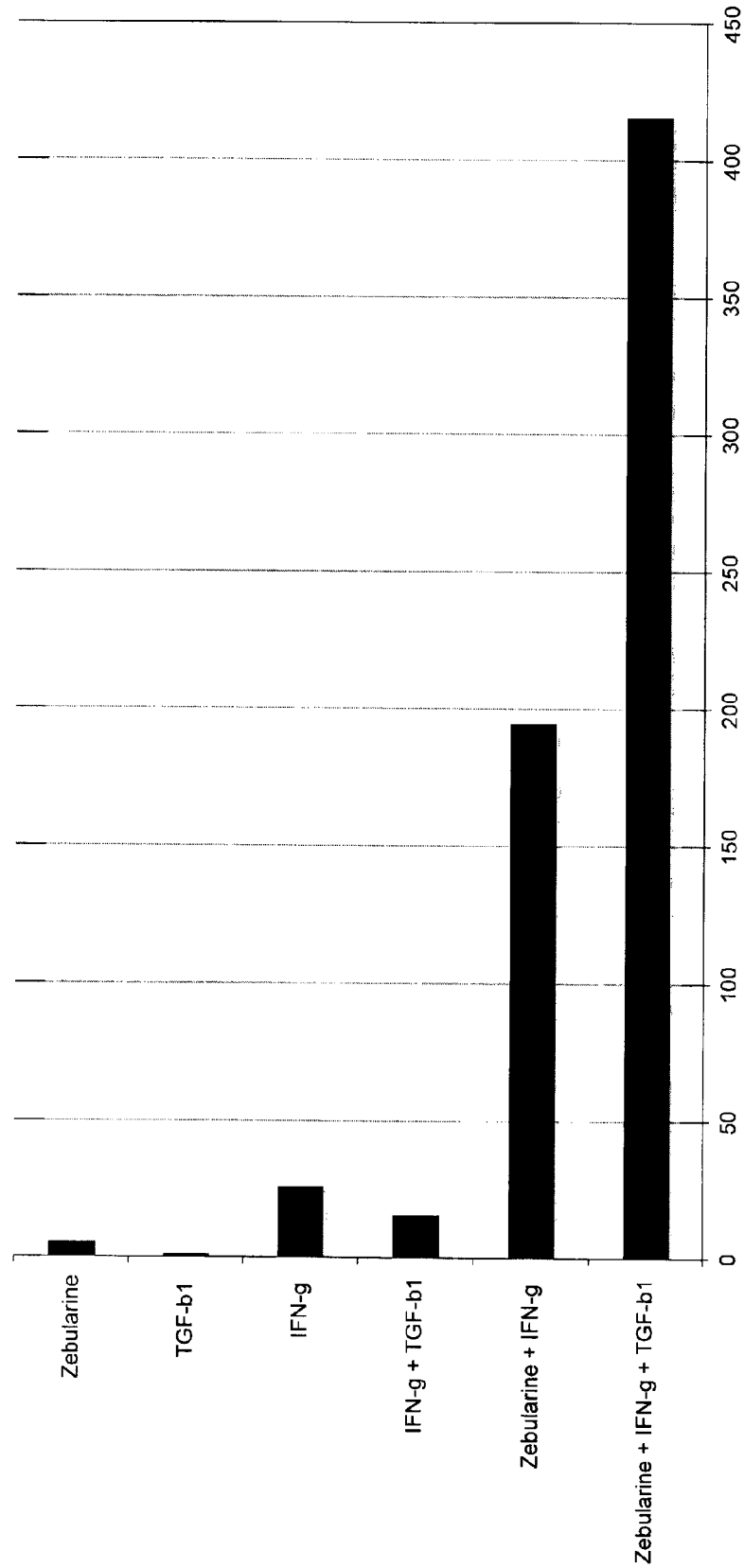

Example 9. Synergistic Effect on IDO Expression by Zebularine, Interferon Gamma and TGF-Beta Materials and methods used were the same as described in Example 1 above. Cells of the human monocytic cell line THP-1 were non-exposed (medium control), exposed to 100 uM zebularine (Berry & Associates, Inc. USA) alone, or to 20 ng/ml tumor growth factor beta 1 (TGF-b1) (Sigma) alone, or to 100 iu/ml interferon gamma (IFN-g), or to a combination of IFN-g and TGF-b1, or to a combination of zebularine and IFN-g, or to a combination of all three substances, zebularine, IFN-g, and TGF-b1. The combination treatment with IFN-g and TGF-b1 was performed by adding IFN-g to the medium 72 h after start of culture and replacing the medium 24 h later with a medium containing TGF-b1. The combination treatment with zebularine and IFN-g was performed by including zebularine in medium from start of culture, after 72 h adding IFN-g and 24 h later replacing the medium with medium containing zebularine. The combined treatment with all three substances was performed by adding zebularine from start of culture, adding IFN-g after 72 h, and after another 24 h replacing the medium with medium containing zebularine and TGF-b1. The treatments with singular substances were performed in the same intervals, and at the end of the interval the medium was replaced with medium without additives. The combination of all three substances induces a strong synergistic effect on IDO1 expression, significantly stronger than zebularine and IFN-g together or each alone (FIG. 9). In contrast, TGF-b1, in the absence of zebularine, reduces the effect of IFN-g. The strong synergistic effect is observed 24 h after removal of IFN-g, indicating a sustained synergistic effect on IDO1 expression.

Figure 10:
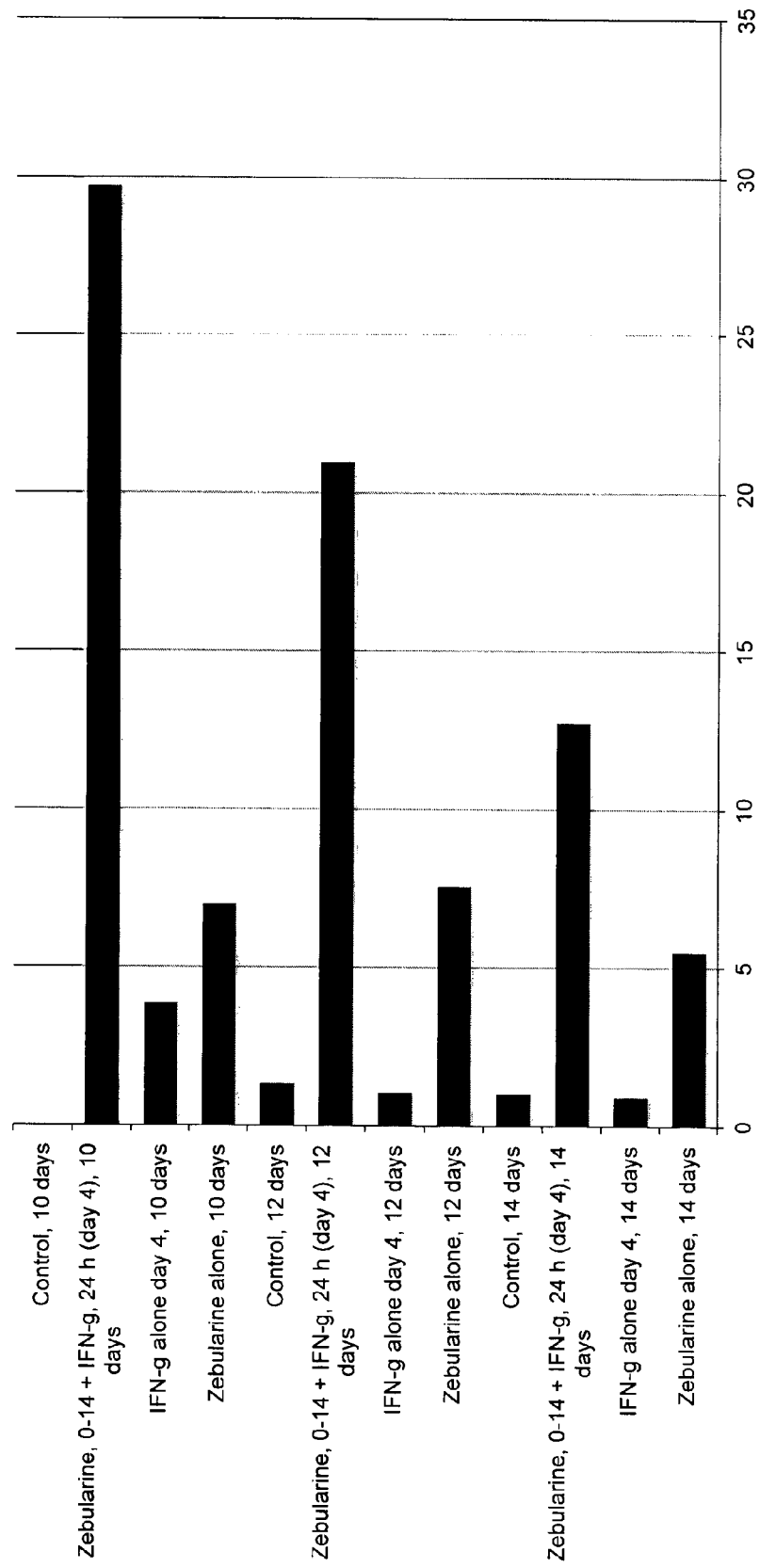
FIG. 10. Sustained synergistic effect on IDO expression by zebularine and a 24 h-exposure to interferon gamma FIG. 11. Sustained synergistic effect on IDO expression by zebularine, interferon gamma and interferon A FIG. 12. Sustained synergistic effect on IDO expression by zebularine, interferon gamma, interferon A and TGF-beta FIG. 13. Enhanced expression of rIdo1 in rat bone marrow derived dendritic cells (BMDC) after a 5-day-exposure to 50 uM zebularine in vitro and an enhanced suppressive function, inhibiting the polyclonal activation of admixed spleen lymphocytes in vitro FIG. 14. Zebubularine, inoculated daily for 7 days intraperitoneally into adult Wistar rats, induces enhanced expression of rIdo1 in the spleen and a suppressed T cell reactivity to polyclonal stimulation in vitro FIG. 15. Suppression of immunological rejection of allotransplanted pancreatic islets beneath the kidney capsule by daily intraperitoneal inoculations of zebularine for 14 days compared to untreated controls. Blood glucose follow up on control rats as an indication of rejection. Figure shows control animal results.

Example 10. Sustained Synergistic Effect on IDO Expression by Zebularine and a 24 h-Exposure to Interferon Gamma Materials and methods used were the same as described in Example 1 above. Cells of the human monocytic cell line THP-1 were non-exposed (medium control), exposed to 100 uM zebularine (Berry & Associates, Inc. USA) alone for the entire culture period, or to 200 iu/ml interferon gamma (IFN-g, Sigma) alone for 24 h (day 4 of culture) after which culture medium was replaced with medium without additives, or to a combination of 100 uM of zebularine for the entire culture period and IFN-g for 24 h on day 4 of culture, after which culture medium was replaced by medium containing zebularine alone (FIG. 10). RNA was isolated after 10, 12 or 14 days of culture and expression of IDO1 was analyzed. Although the expression induced by the 24 h interferon gamma exposure alone is initially strong, it is minimal at the studied time points. In contrast, the synergistic effect when combined with zebularine was sustained for at least 10 days after removal of interferon gamma, being demonstrable still at day 14. This demonstrates that the synergistically induced IDO1 is maintained for a long time even when the interferon gamma exposure is relatively short and the interferon gamma's own effects have since long disappeared.

Figure 11:
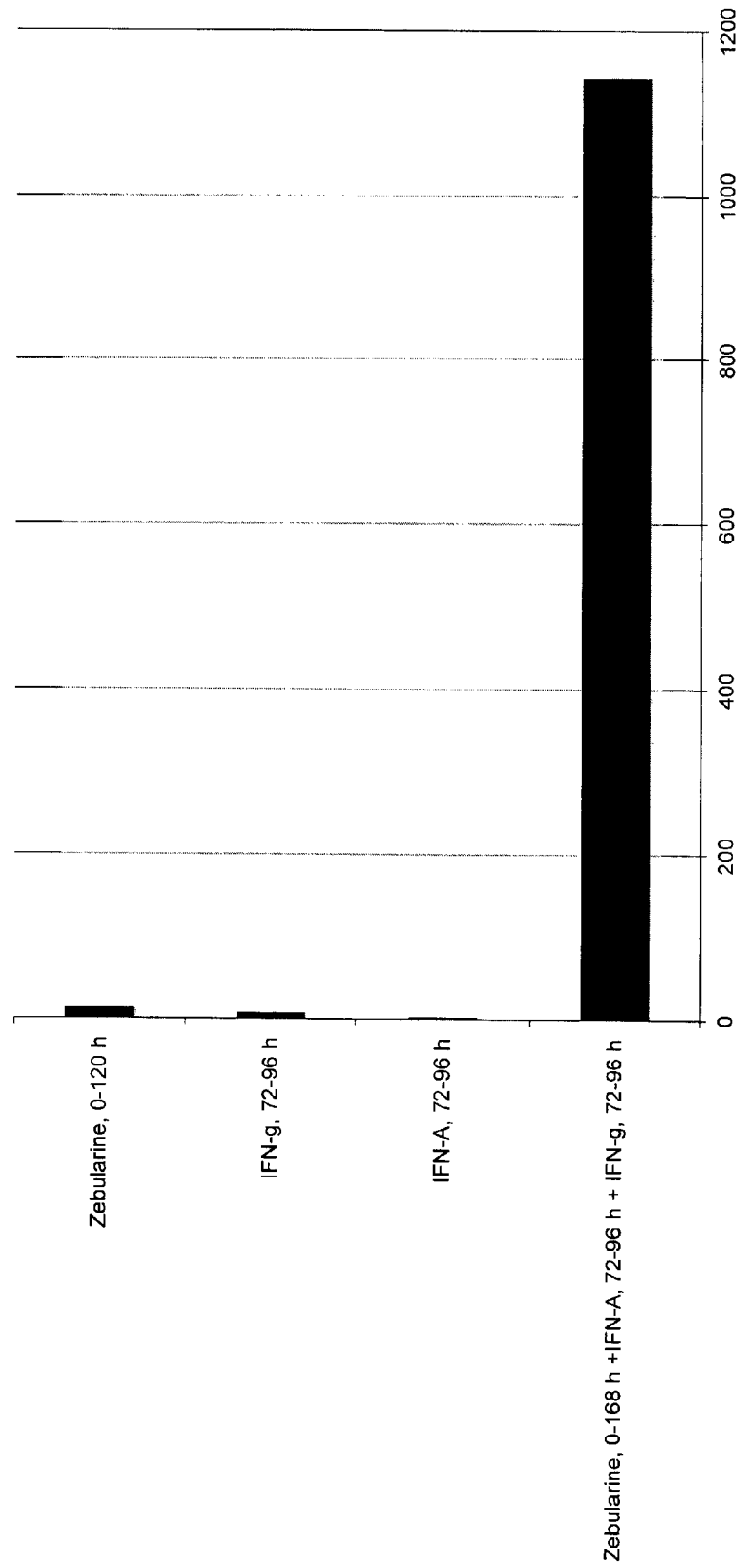

Example 11. Sustained Synergistic Effect on IDO Expression by Zebularine, Interferon Gamma, and Interferon A Materials and methods used were the same as described in Example 1 above. Cells of the human monocytic cell line THP-1 were non-exposed (medium control), exposed to 100 uM zebularine (Berry & Associates, Inc. USA) alone for the entire culture period, or to 100 iu/ml interferon gamma (IFN-g, Sigma) alone for 24 h (day 4 of culture), or to interferon A (IFN-A, Sigma) alone, after which culture medium was replaced with medium without additives. Other cell samples were exposed to a combination of 100 uM zebularine for the entire culture period of 168 h and to IFN-g, and IFN-A for 24 h on day 4 of culture, after which culture medium was replaced by medium containing zebularine alone (FIG. 11). RNA was isolated after 168 h of culture and expression of IDO1 was analyzed. Although the expression induced by the 24 h IFN-g or IFN-A exposure alone is initially strong, it is minimal at the studied time points. In contrast, the synergistic effect when combined with zebularine was sustained for 72 days after removal of the IFN-g and IFN-A. This demonstrates that the synergistically induced strong IDO1 expression is maintained for a long time even when the exposure to IFN-g and IFN-A is relatively short and the own effects of IFN-g and IFN-A have since long disappeared.

Figure 12:
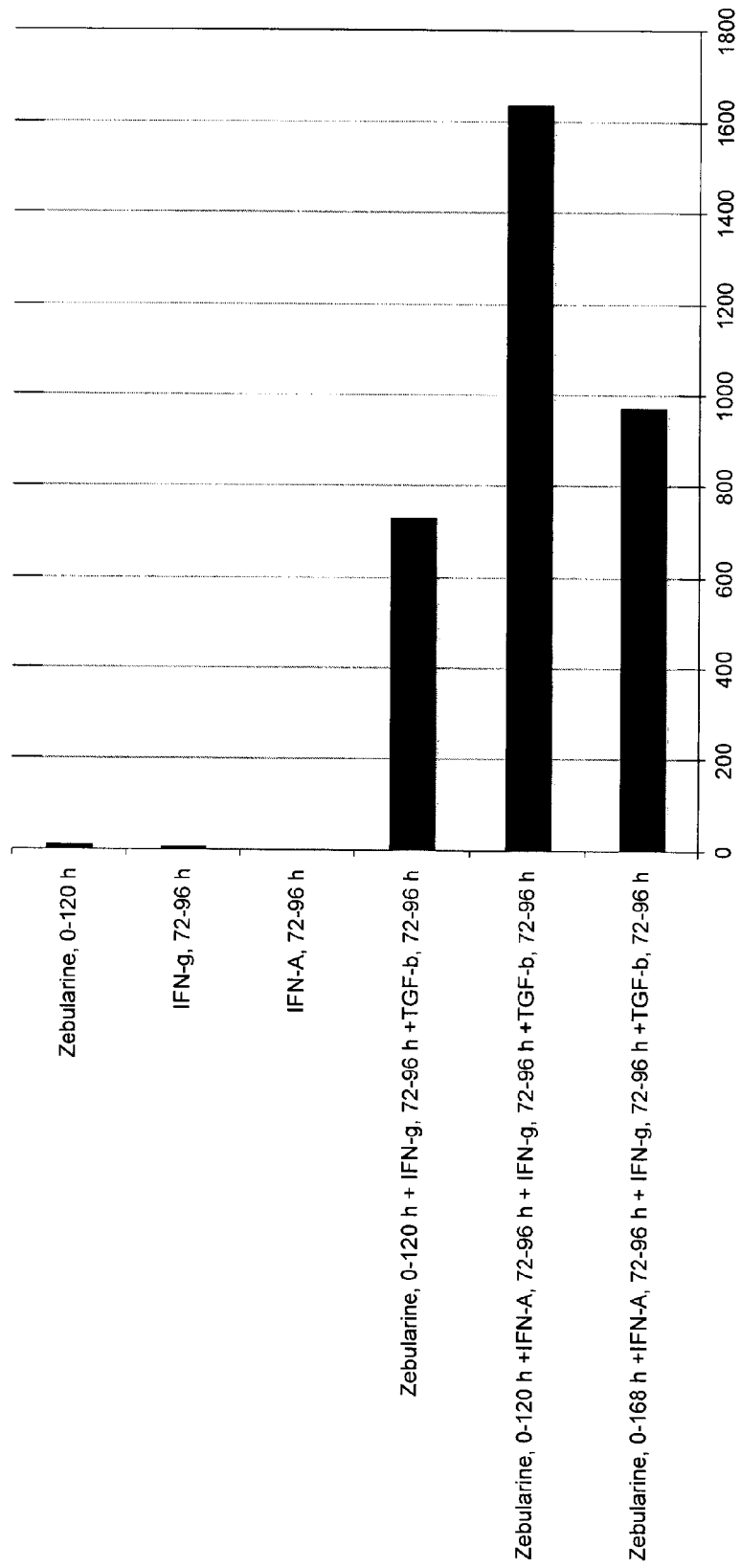

Example 12. Sustained Synergistic IDO Expression by Combined Treatment with Zebularine, Interferon Gamma, Interferon A, and TGF-Beta Materials and methods used were the same as described in Example 1 above. Cells of the human monocytic cell line THP-1 were non-exposed (medium control), exposed to 100 uM zebularine (Berry & Associates, Inc. USA) alone for the entire culture period, or to 100 iu/ml interferon gamma (IFN-g, Sigma) alone, or to 25 ng7 ml interferon A alone, or to 20 ng/ml TGF-beta (TGG-b, Sigma) alone for 24 h (day 4 of culture), after which culture medium was replaced with medium without additives. Other cell samples were exposed to a combination of 100 uM zebularine for the entire culture period of 168 h and to IFN-g, IFN-A, and TGF-b for 24 h on day 4 of culture, after which culture medium was replaced by medium containing zebularine alone (FIG. 12). RNA was isolated after 168 h of culture and expression of IDO1 was analyzed. Although the expression induced by the 24 h IFN-g or IFN-A exposure alone is initially strong, it is minimal at the studied time points. In contrast, the synergistic effect of the 4 substances when combined with zebularine was sustained for 72 days after removal of IFN-g and IFN-A. This demonstrates that the synergistically induced strong IDO1 expression is maintained for a long time even when the exposure to IFN-g and IFN-A and TGF-b is relatively short and the own effects of IFN-g and IFN-A have since long disappeared.

Figure 13:
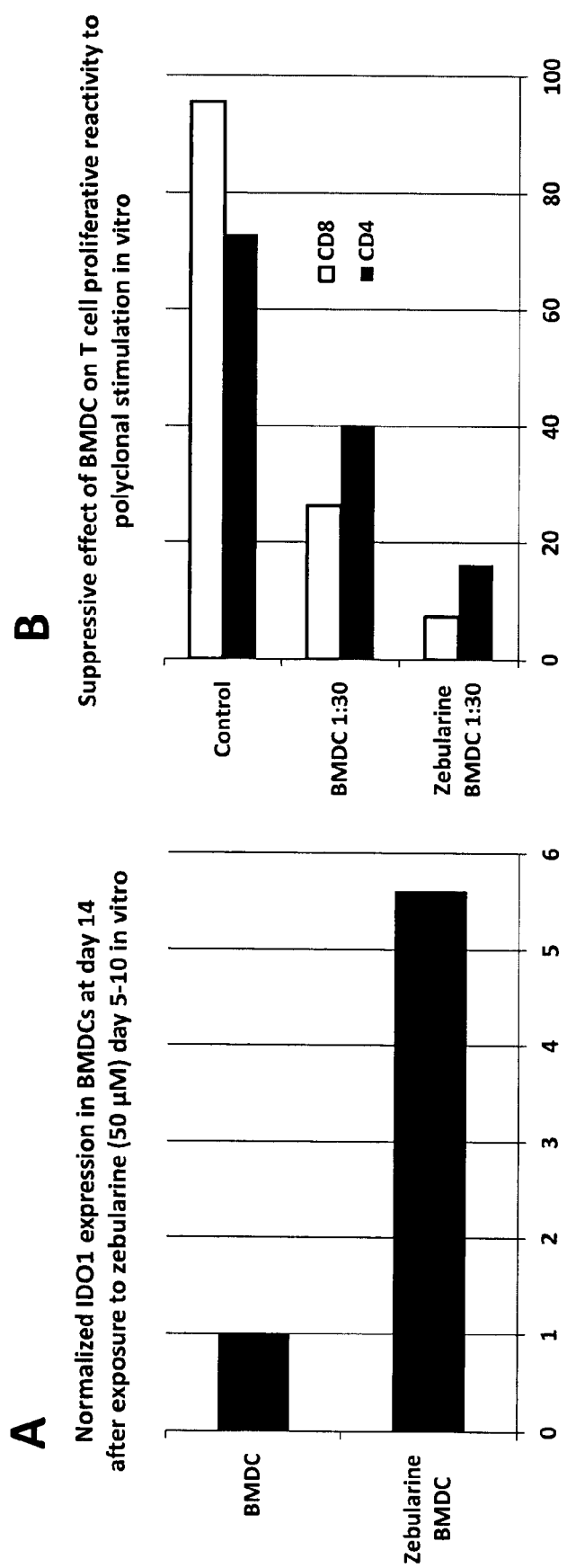

Example 13. Enhanced Expression of IDO in Rat Bone Marrow Derived Dendritic Cells (BMDC) after Exposure to Zebularine In Vitro and an Enhanced Suppressive Function, Inhibiting Immune Reactivity of Admixed Spleen Lymphocytes Bone marrow cells were harvested from the femurs of rats and cultured by established in vitro techniques in the presence of the cytokines IL-4 (5 ng/ml) and GM-CSF (5 ng/ml) to support differentiation into dendritic cells (BMDC) On day 7 of the culture, medium was replaced by medium containing only GM-CSF. Some of the BMDC were exposed to zebularine 50 uM during days 5-10 of culture and control cells were left without this further treatment. The expression of IDO1 by control and zebularine treated cells was analyzed (FIG. 13a). The result demonstrates that zebularine exposure enhances the expression of IDO1 above the level expressed by immature control BMDC. The same two types of cells were also tested for capacity to suppress the proliferative immune response of spleen CD4+ and CD8+ T-cells, respectively, of the same inbred strain of Fischer 344 rats upon stimulation with the strong stimulator anti-CD3 attached to the bottom of culture wells. The proliferation was analyzed in FACS by the CFSE technique and the monoclonal antibodies recognizing the CD4 and CD8 makers. Admixture of zebularine treated BMDC in a proportion of 1:30 to cultures of spleen cells demonstrated a significantly stronger suppressive effect on the proliferative response than the control BMDC tested in parallel, both for CD4+ and for CD8+ T-cells (FIG. 13b). This demonstrates that exposure of BMDC to zebularine in vitro is inducing stronger expression of IDO1, and that these BMDC also have a stronger suppressive effect on T-cell responsiveness than BMDC not exposed to zebularine.

Example 14. Zebularine, Inoculated Daily for 7 Days Intraperitoneally into Adult Rats, Induces Enhanced Expression of IDO in the Spleen and a Suppressed Spleen T Cell Reactivity to Immune Stimulation In Vitro One group of Wistar rats was given intraperitoneal daily inoculations of zebularine (225 mg/kg/day) for 7 days and a parallel control group received intraperitoneal daily inoculations of PBS. RNA was isolated from the spleens and the expression of IDO1 was analyzed by the quantitative RT-PCR technique. The results demonstrate that systemic treatment with zebularine in vivo induces enhanced expression of IDO1 in spleen cells (FIG. 14a). Also, spleen cells from both groups were harvested after the last dose of zebularine and tested for their T cell proliferative reactivity to polyclonal stimulation with anti-CD3 antibodies. The proliferation was analyzed in FACS by the CFSE technique and monoclonal anti-rat CD4 and CD8 antibodies (FIG. 14b). The calculated proliferative response was approximately three times lower with cells from zebularine-treated rats compared to cells from control rats treated with PBS. This demonstrates that zebularine treatment induces enhanced expression of IDO1 in the spleen and inhibited immune responsiveness of spleen T lymphocytes.

Example 15. Suppression of Immunological Rejection of Allotransplanted Pancreatic Islets by Daily Intraperitoneal Inoculations of Zebularine for 14 Days Pancreatic islets were isolated from the pancreas of Lewis rats by established technique. After culture at 37° C. over night, 500-1200 islets were implanted beneath the kidney capsule of adult (11-14 weeks old) Fischer 344 rats that were confirmed hyperglucemic (blood glucose >20 mMol/L) after having received a single dose of 35-40 mg/kg intraperitoneally of Streptozotocine, which is selectively toxic to the insulin producing beta cells present in the pancreatic islets. The blood glucose promptly decreased to normal levels as a sign of successful transplantation of insulin producing islets. One group of these rats was left without further treatment as Controls, whereas another group was treated with intraperitoneal daily inoculations of zebularine (225 mg/kg) for 14 days starting 6-8 days after transplantation at a time when the rats had a normal blood sugar below 11.1 mMol/L. The allotransplanted islets were immunologically rejected within 9-14 days in 6/8 control rats (FIG. 15). The two exceptional rats that maintained a normal blood sugar were subjected to nephrectomy 40 and 43 days after transplantation to check whether their normal blood glucose was a result of unexpected sustained survival of the grafted islets (in which case their blood sugar should promptly increase upon removal of the graft) or was due to a recovery of some Streptozotocinedamaged pancreatic islets (in which case their blood sugar should stay normal despite removal of the graft). Since the blood glucose stayed normal for >7 days after nephrectomy of the two control rats, it was concluded that after the initial damage caused by Streptozotocine in these 2 rats, some pancreatic islets had recovered to produce sufficient amounts of insulin to maintain a normal blood sugar level. Twenty two days after transplantation only 1/10 of the zebularine treated rats had rejected the graft as indicated by a normal blood sugar in all but this single rat at completion of the treatment 20-22 days after transplantation and in all of 7 analyzed >1 week after the zebularine treatment was stopped (FIG. 16). This demonstrates an immunosuppressive or tolerance inducing capacity of the IDO1-inducing substance zebularine.

The invention claimed is:

1. A method of inducing indolamine 2,3-dioxygenase (IDO) in a cell culture, the method comprising:
   (a) providing a cell culture comprising isolated IDO-inducible cells and a suitable medium wherein the isolated IDO-inducible cells are selected from the group consisting of dendritic cells, antigen-presenting cells, and monocytic cells;
   (b) providing a composition comprising
      (i) an effective amount of a first compound being zebularine, which induces IDO by a first mechanism; and
      (ii) an effective amount of a second compound selected from the group consisting of interferon gamma, human chorionic gonadotropine, and interferon alpha, which induces IDO by a second mechanism;
   (c) incubating the cell culture and the composition together; and
   (d) inducing IDO in the incubated cells;
   wherein the composition gives rise to a synergistic effect on the IDO level in the incubated cells compared to the sum of the IDO level individually achieved by the first compound and the second compound.

2. The method according to claim 1, wherein the composition comprises compounds selected from the group consisting of:
   (a) at least interferon gamma and zebularine;
   (b) at least zebularine and human chorionic gonadotropine; and
   (c) at least zebularine and interferon alpha.

3. The method according to claim 1, wherein the composition comprises compounds selected from the group consisting of:
   (a) at least interferon gamma, zebularine, and valproic acid;
   (b) at least interferon gamma, interferon alpha, and zebularine;
   (c) at least interferon gamma, zebularine, and TGF-beta; and
   (d) at least zebularine, interferon alpha, interferon gamma, and TGF-beta.

4. The method according to claim 2, wherein the composition comprises compounds selected from the group consisting of:
   (a) interferon gamma, zebularine, and valproic acid;
   (b) interferon gamma, interferon alpha, and zebularine;
   (c) interferon gamma, zebularine, and TGF-beta;
   (d) zebularine and human chorionic gonadotropine; and
   (e) zebularine, interferon alpha, interferon gamma, and TGF-beta.

5. The method according to claim 1, wherein the medium is RPMI medium.

6. The method according to claim 1, wherein the isolated IDO-inducible cells are dendritic cells or antigen-presenting cells.

7. The method according to claim 1, wherein the isolated IDO-inducible cells are monocytic cells.

8. A cell culture obtained by the method according to claim 1.

9. The method according to claim 2, wherein the composition comprises compounds selected from the group consisting of:
   (a) zebularine and interferon gamma; and
   (b) zebularine and interferon alpha.

10. The method according to claim 2, wherein the isolated IDO-inducible cells are dendritic cells or antigen-presenting cells.

11. The method according to claim 6, wherein the isolated IDO-inducible cells are dendritic cells and wherein said dendritic cells are derived from bone marrow cells by differentiation in vitro.

* * * * *